US012620474B2

(12) United States Patent
Meguro

(10) Patent No.: US 12,620,474 B2
(45) Date of Patent: May 5, 2026

(54) MEDICAL IMAGE PROCESSING APPARATUS, ENDOSCOPE SYSTEM, METHOD OF OPERATING MEDICAL IMAGE PROCESSING APPARATUS, AND NON-TRANSITORY COMPUTER READABLE MEDIUM

(71) Applicant: FUJIFILM Corporation, Tokyo (JP)

(72) Inventor: Misaki Meguro, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 874 days.

(21) Appl. No.: 18/046,788

(22) Filed: Oct. 14, 2022

(65) Prior Publication Data

US 2023/0101620 A1     Mar. 30, 2023

Related U.S. Application Data

(63) Continuation of application No. PCT/JP2021/015712, filed on Apr. 16, 2021.

(30) Foreign Application Priority Data

Apr. 16, 2020     (JP) ................................. 2020-073517

(51) Int. Cl.
*G06V 10/25*     (2022.01)
*G16H 30/20*     (2018.01)

(52) U.S. Cl.
CPC ............. *G16H 30/20* (2018.01); *G06V 10/25* (2022.01)

(58) Field of Classification Search
CPC ........ G16H 30/20; G16H 20/40; G16H 30/40; G16H 50/20; G16H 15/00; G16H 50/50;
(Continued)

(56) References Cited

U.S. PATENT DOCUMENTS 7,260,249 B2 *     8/2007     Smith .................... G16H 30/40
382/128
2012/0183188 A1     7/2012     Moriya
(Continued)

FOREIGN PATENT DOCUMENTS

CN     107205691 A  *     9/2017     ........... A61B 6/5247
CN     106068451 B  *     4/2020     ........... A61B 6/5205
(Continued)

OTHER PUBLICATIONS

An Office Action; "Decision of Refusal," mailed by the Japanese Patent Office on May 28, 2024, which corresponds to Japanese Patent Application No. 2022-515450 and is related to U.S. Appl. No. 18/046,788, with English language translation.
(Continued)

*Primary Examiner* — Jose L Couso
(74) *Attorney, Agent, or Firm* — Studebaker Brackett PLLC

(57)     ABSTRACT

A processor device includes an image signal acquisition unit, an image processing unit, a display control unit, an image storage control unit, and a user input reception unit. The image processing unit detects a region-of-interest, superimposes and displays a highlight display, and performs a setting change from a first highlight level setting value to a second highlight level setting value for changing a shape of the highlight display to be different. The second highlight level setting value is stored together with an endoscopic image.

14 Claims, 14 Drawing Sheets

(58) Field of Classification Search

CPC .. G06V 10/25; G06V 10/143; G06V 2201/03; G06V 30/416; G06V 20/47; G06V 2201/031; G06V 10/764; G06V 20/20; A61B 1/045; A61B 5/055; A61B 8/14; A61B 5/032; A61B 2576/00; A61B 5/00; A61B 5/0013; A61B 6/461; A61B 6/463; A61B 6/468; A61B 6/5294; A61B 6/566; A61B 1/000094; A61B 1/0005; A61B 1/00045; A61B 1/00188; A61B 1/0661; A61B 1/0669; A61B 2017/00199; A61B 90/37; G06T 11/60; G06T 2210/41; G06T 19/00; G06T 7/0012; G06T 7/11; G06F 40/166; G06F 40/169; G06F 18/24; G06F 3/14; G09G 2340/12; G09G 2380/08; G09G 2320/0276; G09G 2354/00; H04N 21/854; H04N 21/8549; H04N 7/18; H04N 23/555; H04N 23/56; H04N 23/635

See application file for complete search history.

(56) References Cited

U.S. PATENT DOCUMENTS

| | | | |
|---|---|---|---|
| 2012/0327205 A1 | 12/2012 | Takahashi | |
| 2013/0258080 A1 | 10/2013 | Kuriyama | |
| 2013/0338493 A1* | 12/2013 | Durvasula | A61B 5/065 600/424 |
| 2017/0231714 A1* | 8/2017 | Kosmecki | A61B 34/10 345/419 |
| 2018/0242817 A1 | 8/2018 | Imaizumi et al. | |
| 2018/0310809 A1 | 11/2018 | Watanabe et al. | |
| 2018/0342060 A1* | 11/2018 | Yao | G06F 40/279 |
| 2019/0114738 A1 | 4/2019 | Sonoda | |
| 2019/0267132 A1 | 8/2019 | Fuchigami et al. | |
| 2019/0279408 A1 | 9/2019 | Hirakawa et al. | |
| 2020/0243184 A1* | 7/2020 | Nagata | G06T 17/20 |
| 2021/0000327 A1 | 1/2021 | Kitamura et al. | |
| 2021/0012495 A1 | 1/2021 | Kamon et al. | |
| 2021/0012870 A1 | 1/2021 | Hirakawa et al. | |

FOREIGN PATENT DOCUMENTS

| | | | | |
|---|---|---|---|---|
| JP | 5541914 B2 | 7/2014 | | |
| JP | 5663283 B2 | 2/2015 | | |
| JP | 2019-149130 A | 9/2019 | | |
| JP | 2019-153249 A | 9/2019 | | |
| WO | 2011/033769 A1 | 3/2011 | | |
| WO | 2017/073338 A1 | 5/2017 | | |
| WO | WO-2017073337 A1 * | 5/2017 | | A61B 1/04 |
| WO | 2017/110459 A1 | 6/2017 | | |
| WO | 2017/216922 A1 | 12/2017 | | |
| WO | WO-2019003911 A1 * | 1/2019 | | G16H 30/40 |
| WO | 2019/146066 A1 | 8/2019 | | |
| WO | 2019/193983 A1 | 10/2019 | | |
| WO | 2019/198637 A1 | 10/2019 | | |
| WO | WO-2019187502 A1 * | 10/2019 | | G06V 10/44 |
| WO | WO-2020059526 A1 * | 3/2020 | | G06V 10/25 |

OTHER PUBLICATIONS

International Search Report issued in PCT/JP2021/015712; mailed Jun. 22, 2021.

International Preliminary Report on Patentability (Chapter I) and Written Opinion of the International Searching Authority issued in PCT/JP2021/015712; issued Oct. 13, 2022.

An Office Action mailed by the Japanese Patent Office on Sep. 5, 2023, which corresponds to Japanese Application No. 2022-515450 with English translation.

An Office Action; "Notice of Reasons for Refusal," mailed by the Japanese Patent Office on Jan. 23, 2024, which corresponds to Japanese Patent Application No. 2022-515450 and is related to U.S. Appl. No. 18/046,788, with English language translation.

* cited by examiner

MEDICAL IMAGE PROCESSING APPARATUS, ENDOSCOPE SYSTEM, METHOD OF OPERATING MEDICAL IMAGE PROCESSING APPARATUS, AND NON-TRANSITORY COMPUTER READABLE MEDIUM

CROSS-REFERENCE TO RELATED APPLICATIONS

This application is a Continuation of PCT International Application No. PCT/JP2021/015712 filed on 16 Apr. 2021, which claims priority under 35 U.S.C § 119(a) to Japanese Patent Application No. 2020-073517 filed on 16 Apr. 2020. The above application is hereby expressly incorporated by reference, in its entirety, into the present application.

BACKGROUND OF THE INVENTION

1. Field of the Invention

The present invention relates to a medical image processing apparatus, an endoscope system, a method of operating a medical image processing apparatus, and a non-transitory computer readable medium containing a program for a medical image processing apparatus capable of detecting a region-of-interest such as a lesion portion.

2. Description of the Related Art

In a medical field, image diagnosis such as diagnosis of a disease of a patient and follow-up are performed by using medical images such as endoscopic images, X-ray images, computed tomography (CT) images, and magnetic resonance (MR) images. Based on such image diagnosis, a doctor or the like make a decision on a treatment policy.

In recent years, in the image diagnosis using medical images, the medical images are analyzed, and regions-of-interest that should be carefully observed such as lesions and tumors in organs are automatically detected. In particular, by performing machine learning such as deep learning, accuracy in detection of the regions-of-interest is dramatically improved.

JP5541914B (corresponding to US2012/0327205A1) and JP5663283B (corresponding to US2013/0258080A1) disclose a medical image processing apparatus that performs image processing based on detection information in a case where a region-of-interest such as a lesion portion is detected from a medical image. In image diagnosis using such a medical image processing apparatus, generally, a region-of-interest is detected from a medical image in real time and a medical image on which a highlight display for highlighting the region-of-interest is superimposed is displayed on a monitor in real time.

SUMMARY OF THE INVENTION

In a case where the medical image processing apparatus described in JP5541914B and JP5663283B is used for image diagnosis, in real time display of the medical image on which the highlight display of the region-of-interest is superimposed, it is important that the highlight display is not too obtrusive so as not to hinder a diagnosis of a doctor. On the other hand, in a case where a medical image is used for viewing of a still image, a report, a presentation material, or the like other than the image diagnosis, a highlight display different from the highlight display in the image diagnosis may be required.

However, in the medical image processing apparatus described in JP5541914B and JP5663283B, the highlight display can be set only in a case where a medical image is displayed in real time for the image diagnosis, and no consideration is given to a highlight display in a case where the medical image is displayed after highlight display of a region-of-interest in the medical image is performed in real time and the medical image is stored. In addition, in a case where the medical image is stored with the settings for real time display, when the medical image is thereafter displayed for viewing of a still image, a report, a presentation material, or the like, the highlight display is inconspicuous. As a result, a doctor may not notice that a region-of-interest exists in the medical image.

An object of the present invention is to provide a medical image processing apparatus, an endoscope system, a method of operating a medical image processing apparatus, and a non-transitory computer readable medium containing a program for a medical image processing apparatus capable of displaying a highlight display of a region-of-interest with different settings in a case where a medical image displayed in image diagnosis is subsequently displayed.

According to an aspect of the present invention, there is provided a medical image processing apparatus including a processor, in which the processor is configured to acquire a medical image, detect a region-of-interest in the medical image, superimpose a highlight display for highlighting the detected region-of-interest on the medical image and display the medical image on which the highlight display is superimposed on a display screen, receive user input information by an input operation of a user, perform a setting change from a first highlight level setting value to a second highlight level setting value by the user input information, the first highlight level setting value being a value for highlighting the region-of-interest in a case where the medical image is displayed on the display screen, and the second highlight level setting value being a value for changing a shape of the highlight display to be different, and associate highlight display information including the second highlight level setting value with the medical image and store the medical image associated with the highlight display information.

Preferably, the processor is configured to change a thickness of a line of a frame shape surrounding the region-of-interest, as a change of the shape of the highlight display, in a case where the setting change from the first highlight level setting value to the second highlight level setting value is performed.

Preferably, the processor is configured to change the number of lines of a frame shape surrounding the region-of-interest, as a change of the shape of the highlight display, in a case where the setting change from the first highlight level setting value to the second highlight level setting value is performed. Further, the processor may be configured to form the frame shape from a plurality of lines having different colors from each other in a case where the setting change to the second highlight level setting value is performed.

Preferably, the highlight display using the second highlight level setting value has a highlight level higher than a highlight level of the highlight display using the first highlight level setting value.

Preferably, the processor is configured to perform the setting change in one stage or a plurality of stages, for the setting change from the first highlight level setting value to the second highlight level setting value.

Preferably, in a case where the user input information is not received, the processor is configured to associate highlight display information including the first highlight level setting value with the medical image and store the medical image associated with the highlight display information, without performing the setting change from the first highlight level setting value.

Preferably, the processor is configured to receive the user input information by an input operation of any one of a keyboard, a pressure detection device, a voice input device, or a touch panel input device.

Preferably, the medical image is an endoscopic image obtained by imaging an observation target by an endoscope, and the processor is configured to receive the user input information by an input operation of an operation button provided on the endo scope.

Preferably, the region-of-interest is a lesion portion, and the highlight display information includes any one of position information of the lesion portion in the medical image, dimensions of the lesion portion, a malignancy or a benignancy of the lesion portion, a degree of progression of the lesion portion, the presence or absence of treatment, a note, a part or an organ in which the lesion portion exists, or patient information.

According to another aspect of the present invention, there is provided an endoscope system including: a light source device; an endoscope; a processor; and a monitor, in which the processor is configured to acquire a medical image, detect a region-of-interest in the medical image, superimpose a highlight display for highlighting the detected region-of-interest on the medical image and display the medical image on which the highlight display is superimposed on the monitor, receive user input information by an input operation of a user, perform a setting change from a first highlight level setting value to a second highlight level setting value by the user input information, the first highlight level setting value being a value for highlighting the region-of-interest in a case where the medical image is displayed on the display screen, and the second highlight level setting value being a value for changing a shape of the highlight display to be different, and associate highlight display information including the second highlight level setting value with the medical image and store the medical image associated with the highlight display information. The light source device emits an illumination light beam for illuminating an observation target. The endoscope includes an imaging sensor which images the observation target illuminated with the illumination light beam. The monitor displays a medical image obtained by performing signal processing on an image signal which is output by the imaging sensor.

According to still another aspect of the present invention, there is provided a method of operating a medical image processing apparatus, the method including: a step of acquiring a medical image; a step of detecting a region-of-interest in the medical image; a step of superimposing a highlight display for highlighting the detected region-of-interest on the medical image and displaying the medical image on which the highlight display is superimposed on a display screen; a step of receiving user input information by an input operation of a user; a step of performing a setting change from a first highlight level setting value to a second highlight level setting value by the user input information, the first highlight level setting value being a value for highlighting the region-of-interest in a case where the medical image is displayed on the display screen, and the second highlight level setting value being a value for changing a shape of the highlight display to be different; and a step of associating highlight display information including the second highlight level setting value with the medical image and storing the medical image associated with the highlight display information.

According to still another aspect of the present invention, there is provided a non-transitory computer readable medium for storing a computer-executable program for functioning a computer as a medical image processing apparatus that acquires a medical image and performs image processing on the medical image, the program causing a computer to realize: a function of acquiring the medical image; a function of detecting a region-of-interest in the medical image; a function of superimposing a highlight display for highlighting the detected region-of-interest on the medical image and displaying the medical image on which the highlight display is superimposed on a display screen; a function of receiving user input information by an input operation of a user; a function of performing a setting change from a first highlight level setting value to a second highlight level setting value by the user input information, the first highlight level setting value being a value for highlighting the region-of-interest in a case where the medical image is displayed on the display screen, and the second highlight level setting value being a value for changing a shape of the highlight display to be different; and a function of associating highlight display information including the second highlight level setting value with the medical image and storing the medical image associated with the highlight display information.

According to the present invention, it is possible to display a highlight display of a region-of-interest with different settings in a case where a medical image displayed in image diagnosis is subsequently displayed.

DESCRIPTION OF THE PREFERRED EMBODIMENTS

First Embodiment

Figure 1:
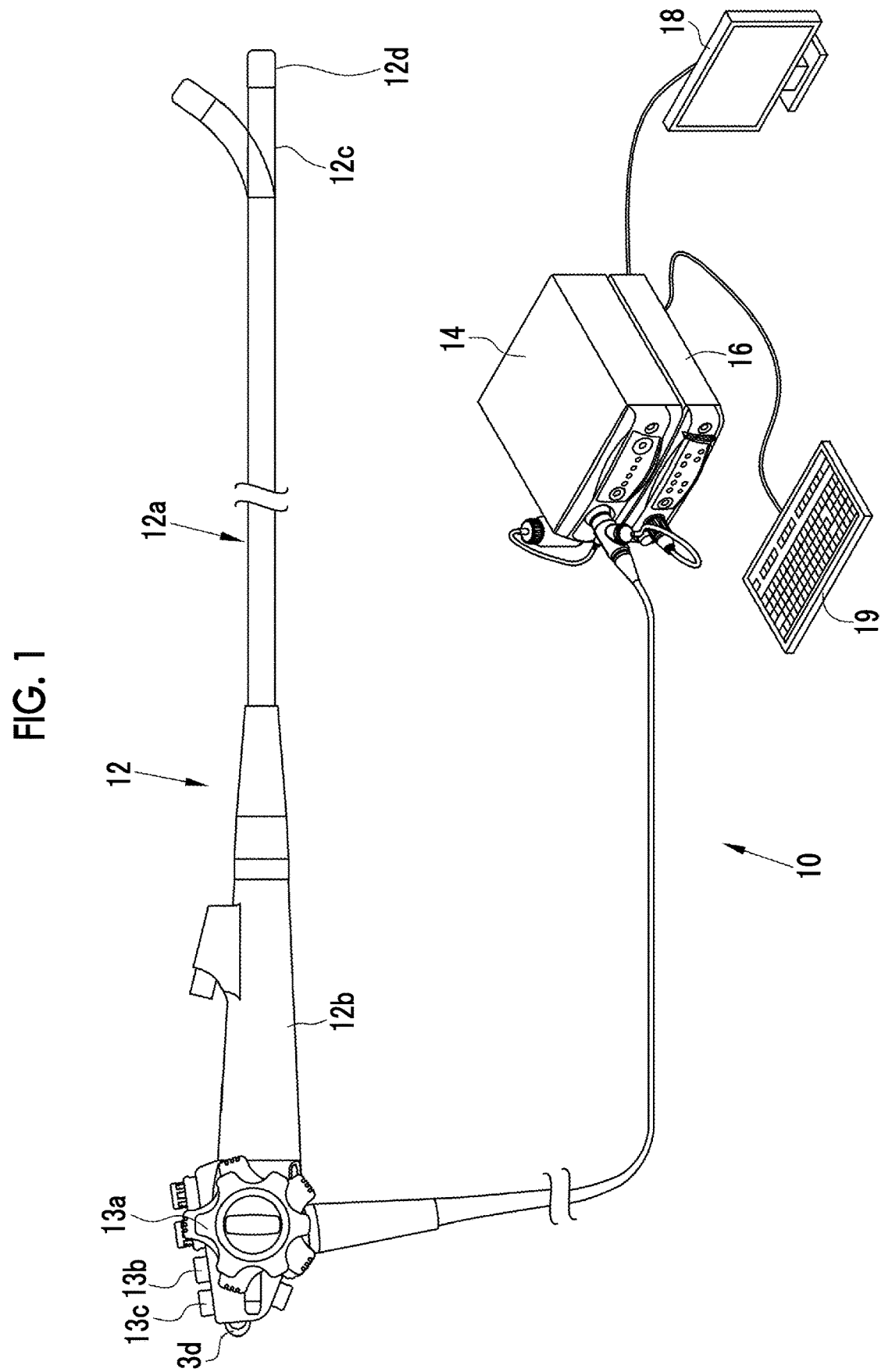
FIG. 1 is an external view of an endoscope system.

As illustrated in FIG. 1, an endoscope system 10 includes an endoscope 12, a light source device 14, a processor device 16, a monitor 18, and a console 19. The endoscope 12 is optically connected to the light source device 14, and is electrically connected to the processor device 16. The endoscope 12 includes an insertion part 12a to be inserted into a body of a subject, an operating part 12b provided at a proximal end portion of the insertion part 12a, and a bendable part 12c and a tip part 12d provided on a distal end side of the insertion part 12a. In a case where an angle knob 13a of the operating part 12b is operated, a bending operation of the bendable part 12c is performed. By the bending operation, the tip part 12d is directed in a desired direction.

The tip part 12d includes an illumination window, an observation window, an air supply/water supply nozzle, and a forceps outlet on a distal end surface (all not illustrated). The illumination window is for irradiating an observation portion with an illumination light beam. The observation window is for taking in a light beam from the observation portion. The air supply/water supply nozzle is for cleaning the illumination window and the observation window. The forceps outlet is for performing various treatments using a forceps and a treatment tool such as an electric scalpel.

In addition to the angle knob 13a, the operating part 12b includes a freeze switch 13b used for a still image acquisition operation, a mode switching unit 13c used for an observation mode switching operation, and a zoom operating part 13d used for a zoom magnification changing operation. The freeze switch 13b can perform a freeze operation for displaying a still image of an observation target on the monitor 18 and a release operation for storing the still image in a storage.

In a case where a user operates the freeze switch 13b, a still image of an observation target is freeze-displayed on the monitor 18, and an alert sound (for example, "pee") indicating that a still image is acquired is emitted. In addition, an image storage instruction is output to the image storage control unit 55 or the like, and the still images of the endoscopic images that are obtained before or after the operation timing of the freeze switch 13b are stored in the image storage unit 56 (refer to FIG. 2) of the processor device 16.

The image storage unit 56 is a storage unit such as a hard disk or a USB (Universal Serial Bus) memory. An operation device other than the freeze switch 13b may be used to input an image storage instruction. For example, in a case where a foot pedal is connected to the processor device 16 and a user operates the foot pedal (not illustrated) with a foot, an image storage instruction may be input. By using the foot pedal, mode switching may also be performed. In addition, an image storage instruction may be input or mode switching may be performed by voice input, line-of-sight input, a gesture input, or the like.

The endoscope system 10 has a normal mode, a special mode, and a region-of-interest detection mode as observation modes. In a case where the observation mode is the normal mode, a normal light beam obtained by combining light beams having a plurality of colors at a normal-mode light quantity ratio Lc is emitted. Further, in a case where the observation mode is the special mode, a special light beam obtained by combining light beams having a plurality of colors at a light quantity ratio for the special mode Ls is emitted.

Further, in a case where the observation mode is the region-of-interest detection mode, an illumination light beam for the region-of-interest detection mode is emitted. In the present embodiment, as the illumination light beam for the region-of-interest detection mode, the normal light beam is emitted. On the other hand, the special light beam may be emitted.

The processor device 16 is electrically connected to the monitor 18 and the console 19. The monitor 18 outputs and displays an image of the observation target, information related to the image, and the like. The console 19 functions as a user interface that receives an input operation such as designation of a region-of-interest (ROI) or function setting.

Figure 2:
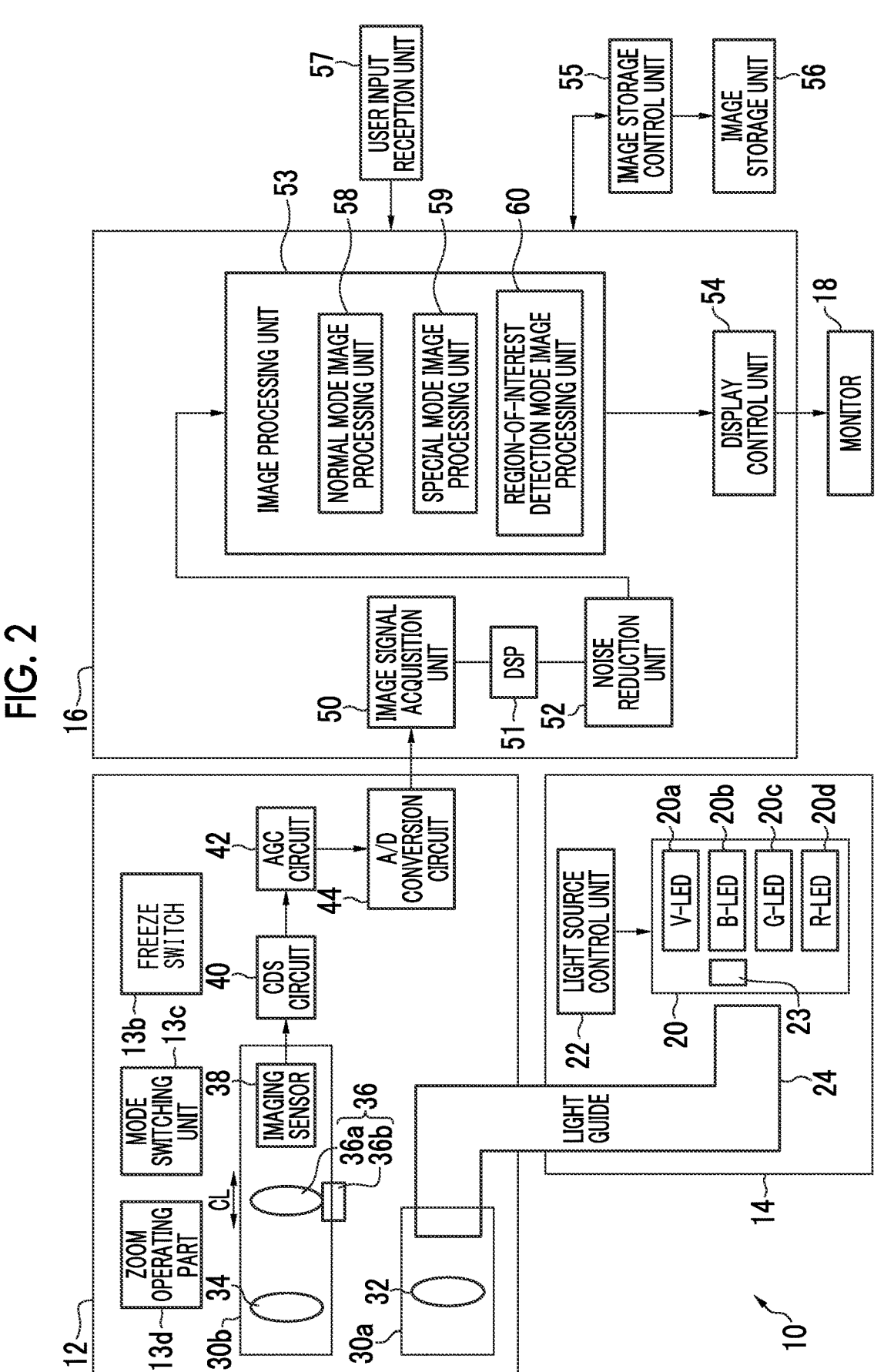
FIG. 2 is a block diagram illustrating a function of the endoscope system according to a first embodiment.

As illustrated in FIG. 2, the light source device 14 includes a light source unit 20 that emits an illumination light beam used for illuminating an observation target, and a light source control unit 22 that controls the light source unit 20. The light source unit 20 is a semiconductor light source such as a light emitting diode (LED) which emits light beams having a plurality of colors. The light source control unit 22 controls a light emission amount of the illumination light beams by turning ON/OFF the LEDs or adjusting a drive current or a drive voltage of the LEDs. Further, the light source control unit 22 controls a wavelength range of the illumination light beams by changing an optical filter or the like.

Figure 3:
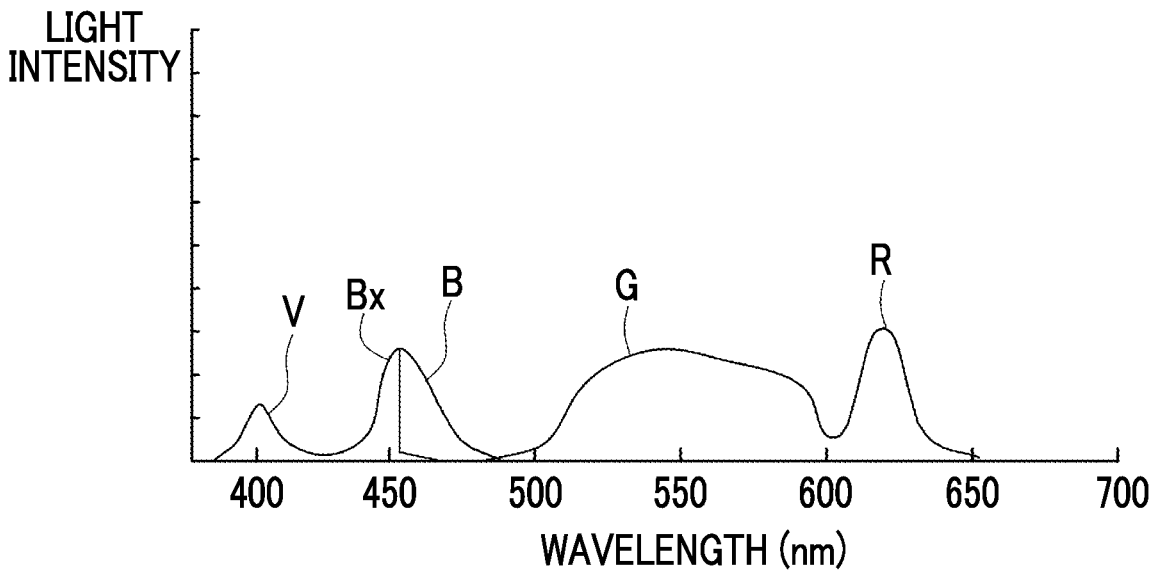
FIG. 3 is a graph illustrating spectral spectra of a violet light beam V, a blue light beam B, a blue light beam Bx, a green light beam G, and a red light beam R.

In the first embodiment, the light source unit 20 includes four-color LEDs of a violet light emitting diode (V-LED) 20a, a blue light emitting diode (B-LED) 20b, a green light emitting diode (G-LED) 20c, and a red light emitting diode (R-LED) 20d and a wavelength cut filter 23. As illustrated in FIG. 3, the V-LED 20a emits a violet light beam V in a wavelength range of 380 nm to 420 nm.

The B-LED 20b emits a blue light beam B in a wavelength range of 420 nm to 500 nm. In the blue light beams B emitted from the B-LED 23b, at least a light beam having a wavelength longer than a peak wavelength of 450 nm is cut by the wavelength cut filter 23. Thereby, the blue light beam Bx passing through the wavelength cut filter 23 is within a wavelength range of 420 to 460 nm. The reason why the light beam in a wavelength range including wavelengths longer than 460 nm is cut in this way is that the light beam in a wavelength range including wavelengths longer than 460 nm causes a decrease in vascular contrast of a blood vessel as an observation target. The wavelength cut filter 23 may dim the light beam in a wavelength range including wavelengths longer than 460 nm instead of cutting the light beam in a wavelength range including wavelengths longer than 460 nm.

The G-LED 20c emits a green light beam G in a wavelength range of 480 nm to 600 nm. The R-LED 20d emits a red light beam R in a wavelength range of 600 nm to 650 nm. In the light beams emitted from the LEDs 20a to 20d, central wavelengths and peak wavelengths may be the same, or may be different from each other.

The light source control unit 22 adjusts a light emission timing, a light emission period, a light emission amount, and a spectral spectrum of the illumination light beams by independently controlling ON/OFF of each of the LEDs 20a to 20d, a light emission amount of each of the LEDs in an ON state, or the like. The light source control unit 22 controls ON/OFF of the LEDs depending on the observation mode. The reference brightness can be set by a brightness setting unit of the light source device 14, the console 19, or the like.

Figure 4:
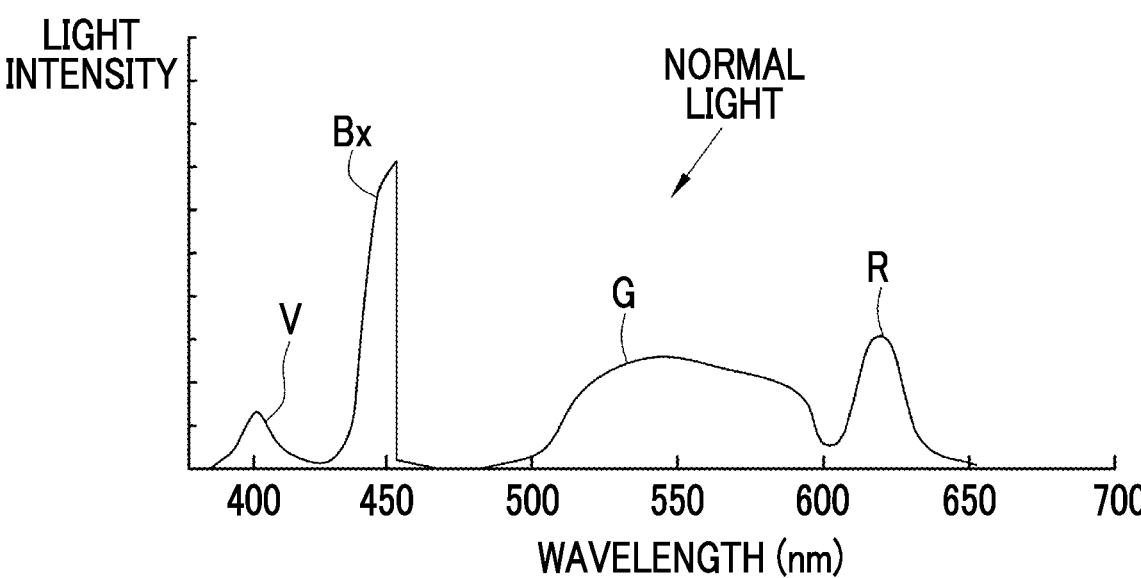
FIG. 4 is a graph illustrating a spectral spectrum of a normal light beam according to the first embodiment.

In a case of the normal mode or the region-of-interest detection mode, the light source control unit 22 turns on all the V-LED 20a, the B-LED 20b, the G-LED 20c, and the R-LED 20d. At that time, as illustrated in FIG. 4, a light quantity ratio Lc between the violet light beam V, the blue light beam B, the green light beam G, and the red light beam R is set such that a peak of a light intensity of the blue light beam Bx is higher than a peak of a light intensity of any one of the violet light beam V, the green light beam G, or the red light beam R. Thereby, in the normal mode or the region-of-interest detection mode, the light beams for the normal mode or the region-of-interest detection mode that have the plurality of colors and include the violet light beam V, the blue light beam Bx, the green light beam G, and the red light beam R are emitted from the light source device 14, as the normal light beams. The normal light beam is almost white because the normal light beam has an intensity of a certain level or higher from a blue wavelength range to a red wavelength range.

Figure 5:
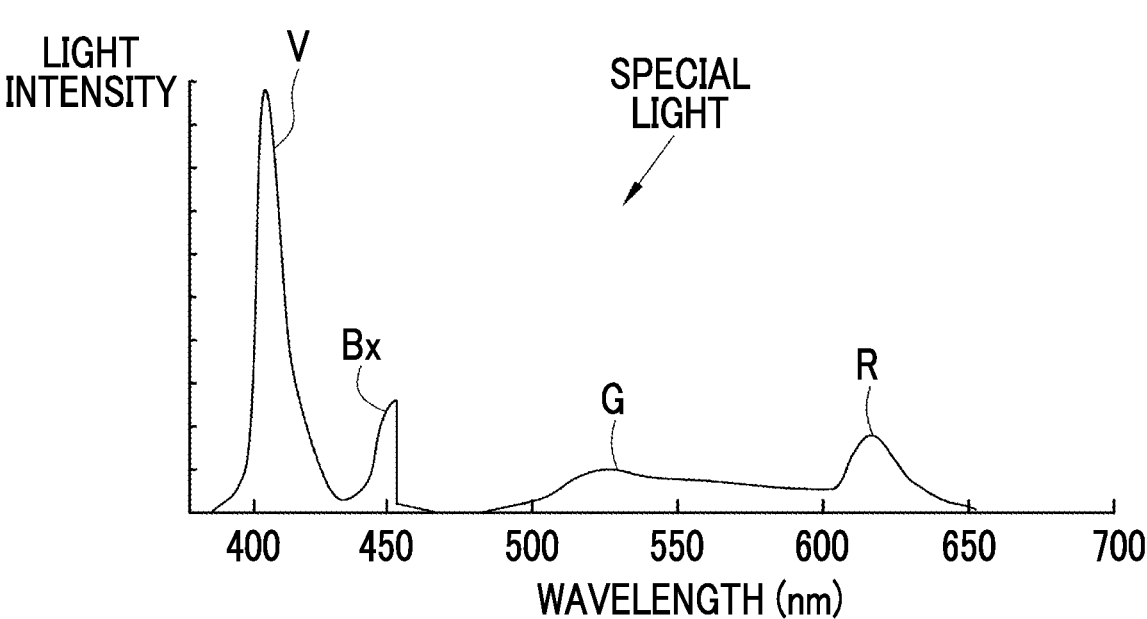
FIG. 5 is a graph illustrating a spectral spectrum of a special light beam according to the first embodiment.

In a case of the special mode, the light source control unit 22 turns on all the V-LED 20a, the B-LED 20b, the G-LED 20c, and the R-LED 20d. At that time, as illustrated in FIG. 5, a light quantity ratio Ls between the violet light beam V, the blue light beam B, the green light beam G, and the red light beam R is set such that a peak of a light intensity of the violet light beam V is higher than a peak of a light intensity of any one of the blue light beam Bx, the green light beam G, or the red light beam R. Further, the peaks of the light intensities of the green light beam G and the red light beam R are set to be lower than the peaks of the light intensities of the violet light beam V and the blue light beam Bx. Thereby, in the special mode, the light beams for the special mode that have the plurality of colors and include the violet light beam V, the blue light beam Bx, the green light beam G, and the red light beam R are emitted from the light source device 14, as the special light beams. The special light beam is bluish because a proportion of the violet light beams V is high. The special light beam may not include light beams having all four colors, and may include at least a light beam from a one-color LED among the four-color LEDs 20a to 20d. Further, preferably, the special light beam has a main wavelength range, for example, a peak wavelength or a central wavelength within a range of 450 nm or lower.

As illustrated in FIG. 2, the illumination light beam emitted by the light source unit 20 is incident on a light guide 24 inserted into the insertion part 12a via an optical path coupling unit (not illustrated) formed by a mirror, a lens, and the like. The light guide 24 is incorporated in the endoscope 12 and the universal cord, and propagates the illumination light beam to the tip part 12d of the endoscope 12. The universal cord is a cord that connects the endoscope 12, the light source device 14, and the processor device 16. As the light guide 24, a multi-mode fiber can be used. As an example, for the light guide 24, a fine fiber cable having a core diameter of 105 μm, a clad diameter of 125 μm, and a diameter of φ0.3 mm to φ0.5 mm including a protective layer serving as an outer skin can be used.

An illumination optical system 30a and an imaging optical system 30b are provided at the tip part 12d of the endoscope 12. The illumination optical system 30a includes an illumination lens 32. The observation target is illuminated with the illumination light beam propagating through the light guide 24 via the illumination lens 32. The imaging optical system 30b includes an objective lens 34, a magnification optical system 36, and an imaging sensor 38 (corresponding to "imaging unit" according to the present invention). Various light beams such as a reflected light beam, a scattered light beam, and a fluorescent light beam from the observation target are incident on the imaging sensor 38 via the objective lens 34 and the magnification optical system 36. Thereby, an image of the observation target is formed on the imaging sensor 38.

The magnification optical system 36 includes a zoom lens 36a that magnifies the observation target and a lens driving unit 36b that moves the zoom lens 36a in an optical axis direction CL. The zoom lens 36a is freely moved between a telephoto end and a wide end according to zoom control by the lens driving unit 36b. Thereby, the observation target imaged on the imaging sensor 38 is magnified or reduced.

The imaging sensor 38 is a color imaging sensor that images the observation target irradiated with the illumination light beam. For each pixel of the imaging sensor 38, any one of an R (red) color filter, a G (green) color filter, or a B (blue) color filter is provided. The imaging sensor 38 receives light beams including a violet light beam to a blue light beam from a B pixel for which the B color filter is provided, receives a green light beam from a G pixel for which the G color filter is provided, and receives a red light beam from an R pixel for which the R color filter is provided. Then, an image signal of each of RGB colors is output from each color pixel. The imaging sensor 38 transmits the output image signal to a CDS circuit 40.

In the normal mode or the region-of-interest detection mode, the imaging sensor 38 outputs a Bc image signal from the B pixel, outputs a Gc image signal from the G pixel, and outputs an Rc image signal from the R pixel by imaging the observation target illuminated with the normal light beam. Further, in the special mode, the imaging sensor 38 outputs a Bs image signal from the B pixel, outputs a Gs image signal from the G pixel, and outputs an Rs image signal from the R pixel by imaging the observation target illuminated with the special light beam.

As the imaging sensor 38, a charge coupled device (CCD) imaging sensor, a complementary metal-oxide semiconductor (CMOS) imaging sensor, or the like can be used. Further, instead of the imaging sensor 38 provided with RGB primary color filters, a complementary color imaging sensor provided with complementary color filters for C (cyan), M (magenta), Y (yellow), and G (green) may be used. In a case where a complementary color imaging sensor is used, image signals of four colors of CMYG are output. Thus, by converting the image signals of four colors of CMYG into image signals of three colors of RGB by complementary-color-to-primary-color conversion, an image signal of each of RGB colors can be obtained as in the imaging sensor 38. Further, instead of the imaging sensor 38, a monochrome sensor without a color filter may be used.

The CDS circuit 40 performs correlated double sampling (CDS) on the analog image signal received from the imaging sensor 38. The image signal that passes through the CDS circuit 40 is input to an AGC circuit 42. The AGC circuit 42 performs automatic gain control (AGC) on the input image signal. An analog to digital (A/D) conversion circuit 44 converts the analog image signal that passes through the AGC circuit 42 into a digital image signal. The A/D conversion circuit 44 inputs the digital image signal after the A/D conversion to the processor device 16.

As illustrated in FIG. 2, the processor device 16 includes an image signal acquisition unit 50, a digital signal processor (DSP) 51, a noise reduction unit 52, an image processing unit 53, a display control unit 54, an image storage control unit 55, an image storage unit 56, and a user input reception unit 57.

The processor device 16 functions as a medical image processing apparatus. As will be described later, the image processing unit 53 acquires an endoscopic image, and detects a region-of-interest in the observation target from the endoscopic image. The display control unit 54 performs highlight display of the region-of-interest on the endoscopic image.

The image signal acquisition unit 50 acquires, from the endoscope 12, a digital image signal corresponding to the observation mode. In a case of the normal mode or the region-of-interest detection mode, a Bc image signal, a Gc image signal, and an Rc image signal are acquired. In a case of the special mode, a B s image signal, a Gs image signal, and an Rs image signal are acquired. In a case of the region-of-interest detection mode, when the observation target is illuminated with the normal light beam, a Bc image signal, a Gc image signal, and an Rc image signal for one frame are acquired, and when the observation target is illuminated with the special light beam, a Bs image signal, a Gs image signal, and an Rs image signal for one frame are acquired.

The DSP 51 performs various signal processing such as defect correction processing, offset processing, DSP gain correction processing, linear matrix processing, gamma conversion processing, and demosaicing processing on the image signal acquired by the image signal acquisition unit 50. The defect correction processing corrects a signal of a defective pixel of the imaging sensor 38. The offset processing sets an accurate zero level by removing a dark current component from the image signal after the defect correction processing. The DSP gain correction processing adjusts a signal level by multiplying the image signal after the offset processing by a specific DSP gain.

The linear matrix processing enhances a color reproducibility of the image signal after the DSP gain correction processing. The gamma conversion processing adjusts brightness and chroma saturation of the image signal after the linear matrix processing. The demosaicing processing (also referred to as smoothing processing or interpolation processing) is performed on the image signal after the gamma conversion processing, and thus a signal of a color which is insufficient in each pixel is generated by interpolation. By the demosaicing processing, all the pixels have signals of each color of RGB colors. The noise reduction unit 52 reduces noise by performing noise reduction processing by, for example, a movement average method, a median filter method, or the like on the image signal after the demosaicing processing and the like by the DSP 51. The image signal after the noise reduction is input to the image processing unit 53.

The image processing unit 53 includes a normal mode image processing unit 58, a special mode image processing unit 59, and a region-of-interest detection mode image processing unit 60. The normal mode image processing unit 58 operates in a case where the normal mode is set, and performs color conversion processing, color enhancement processing, and structure enhancement processing on the Bc image signal, the Gc image signal, and the Rc image signal which are received. In the color conversion processing, color conversion processing including 3×3 matrix processing, gradation transformation processing, three-dimensional look up table (LUT) processing, and the like is performed on the RGB image signal.

The color enhancement processing is performed on the RGB image signal after the color conversion processing. The structure enhancement processing is processing for enhancing a structure of the observation target, and is performed on the RGB image signal after the color enhancement processing. A normal image can be obtained by performing various image processing and the like as described above. Since the normal image is an image obtained based on the normal light beam in which the violet light beam V, the blue light beam Bx, the green light beam G, and the red light beam R are well balanced, the normal image has a natural hue. The normal image is input to the display control unit 54.

The special mode image processing unit 59 operates in a case where the special mode is set. The special mode image processing unit 59 performs color conversion processing, color enhancement processing, and structure enhancement processing on the Bs image signal, the Gs image signal, and the Rs image signal which are received. The processing contents of the color conversion processing, the color enhancement processing, and the structure enhancement processing are the same as the processing contents in the normal mode image processing unit 58. A special image can be obtained by performing various image processing as described above. The special image is an image obtained based on the special light beam in which the light emission amount of the violet light beam V is larger than the light emission amounts of the blue light beam Bx, the green light beam G, and the red light beam R of other colors, the violet light beam having a high absorption coefficient of hemoglobin in a blood vessel. Thus, a resolution of a vascular structure or a ductal structure is higher than a resolution of another structure. The special image is input to the display control unit 54.

Figure 6:
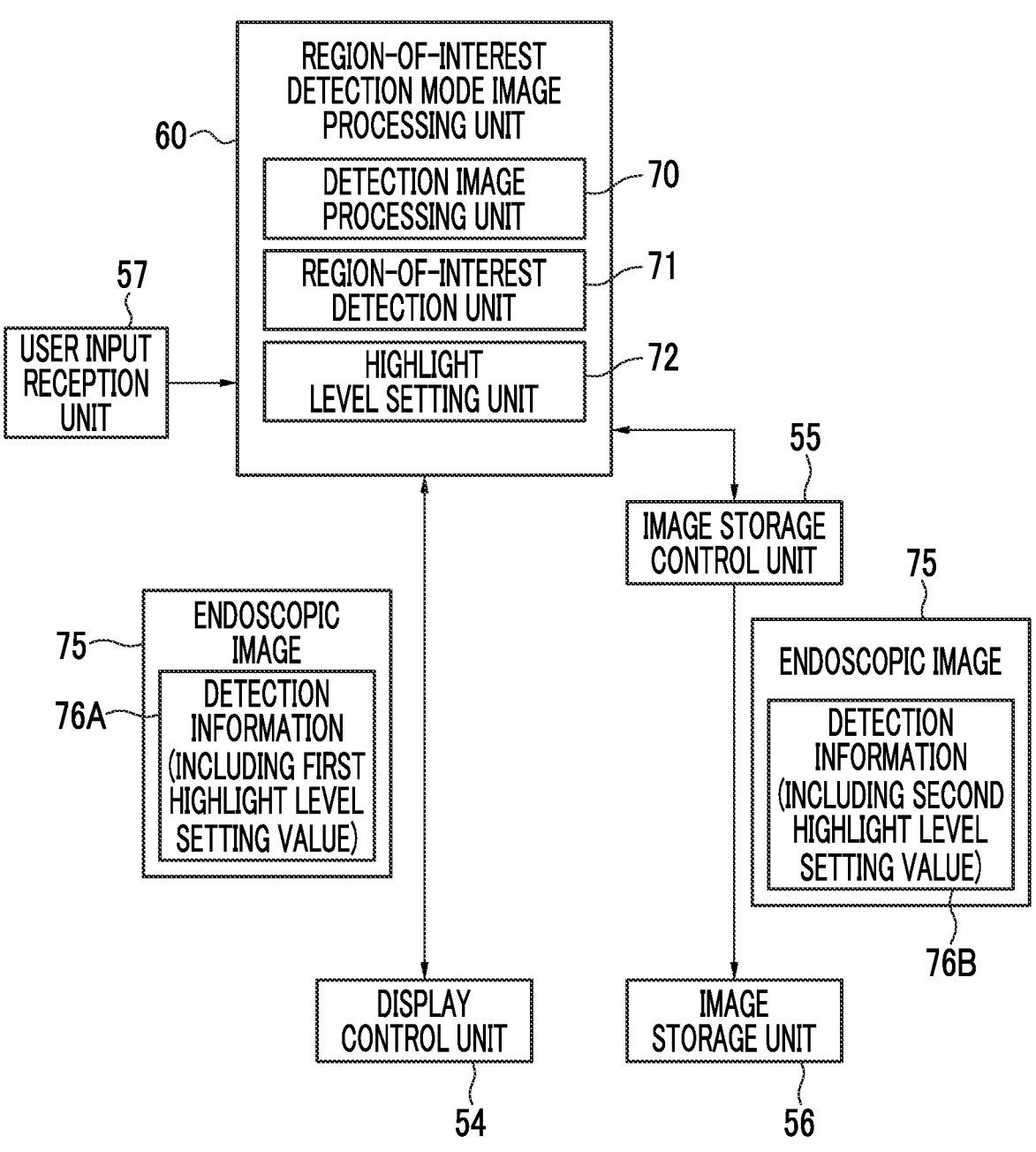
FIG. 6 is a block diagram illustrating functions of a region-of-interest detection mode image processing unit, a display control unit, and an image storage control unit.

The region-of-interest detection mode image processing unit 60 operates in a case where the region-of-interest detection mode is set. As illustrated in FIG. 6, the region-of-interest detection mode image processing unit 60 includes a detection image processing unit 70, a region-of-interest detection unit 71, and a highlight level setting unit 72. The detection image processing unit 70 sequentially acquires an endoscopic image 75 by performing the same image processing as the processing in the normal mode image processing unit 58, such as color conversion processing, on the Bc image signal, the Gc image signal, and the Rc image signal which are received.

The region-of-interest detection unit 71 analyzes the endoscopic image 75, and performs region-of-interest detection processing for detecting a region-of-interest in the observation target. In the present embodiment, the region-of-interest detection unit 71 detects, as a region-of-interest, a lesion portion (for example, a tumor, inflammation, or the like) in the observation target. In this case, the region-of-interest detection unit 71 first divides the endoscopic image 75 into a plurality of small regions, for example, square regions for the number of pixels. Next, an image feature amount is calculated from the divided endoscopic image 75. Subsequently, based on the calculated feature amount, rec- ognition processing as to whether or not each small region is a lesion portion is performed. As the recognition process- ing, preferably, a machine learning algorithm such as a convolutional neural network or deep learning is used.

Further, the feature amount calculated from the endo- scopic image 75 by the region-of-interest detection unit 71 is preferably a value obtained from a shape or a color of a predetermined portion of the observation target or a value obtained from the shape and the color. For example, as the feature amount, preferably, at least one of a density of a blood vessel, a shape of a blood vessel, the number of branches of a blood vessel, a thickness of a blood vessel, a length of a blood vessel, a tortuosity of a blood vessel, a reaching depth of a blood vessel, a shape of a duct, a shape of an opening of a duct, a length of a duct, a tortuosity of a duct, or color information, or a value obtained by combining two or more of these values is used.

Finally, a group of small regions identified as the same type is extracted as one lesion portion. The region-of-interest detection unit 71 records detection information 76A, which includes pieces of information such as position information and dimensions of the extracted lesion portion, a lesion type, and the like, as association information of the endoscopic image 75.

The highlight level setting unit 72 sets a first highlight level setting value and a second highlight level setting value for highlighting the region-of-interest which is detected by the region-of-interest detection mode image processing unit 60. The first highlight level setting value is a highlight level setting value for highlighting the region-of-interest in a real-time display in a case where the highlight display is superimposed on the endoscopic image 75 and the endo- scopic image 75 on which the highlight display is superim- posed is displayed on the monitor 18. On the other hand, the second highlight level setting value is a highlight level setting value which is stored by being associated with the endoscopic image 75 in a case of storing the endoscopic image 75 in the image storage unit 56.

In a case where real-time display is performed in the region-of-interest detection mode, the highlight level setting unit 72 outputs the endoscopic image 75 associated with the first highlight level setting value to the display control unit 54. In this case, the first highlight level setting value is included in the detection information 76A.

The display control unit 54 performs display control for displaying the image or data from the image processing unit 53 on the monitor 18. In a case where the normal mode is set, the display control unit 54 performs control to display the normal image on the monitor 18. In a case where the special mode is set, the display control unit 54 performs control to display the special image on the monitor 18.

Figure 7:
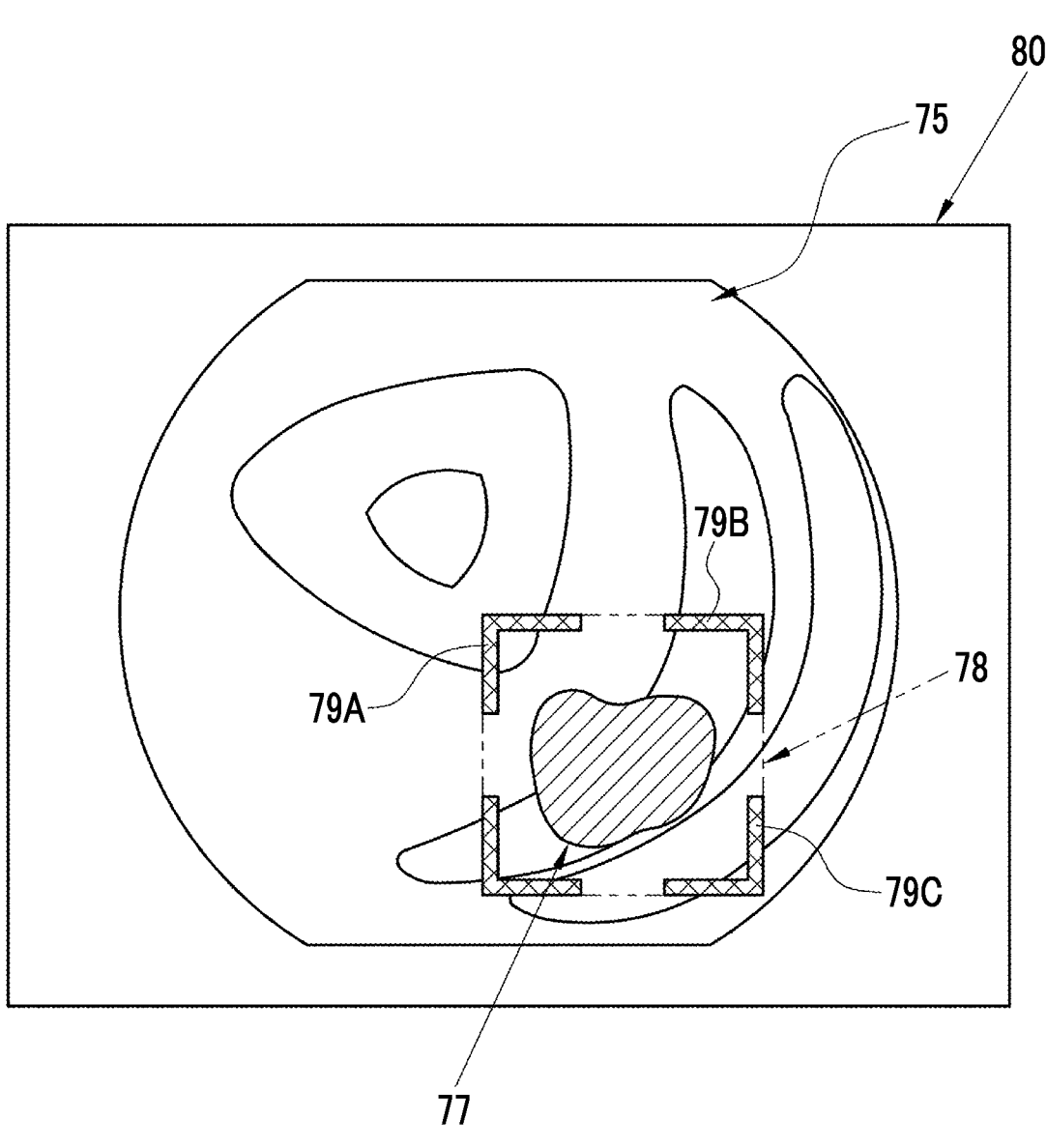
FIG. 7 is an explanatory diagram illustrating an example of a display screen for performing highlight display of a region-of-interest.

In a case where the region-of-interest detection mode is set, the display control unit 54 performs real time display of highlighting the region-of-interest on the endoscopic image 75 based on the endoscopic image 75 output from the region-of-interest detection mode image processing unit 60 and the detection information 76A recorded as the association information of the endoscopic image 75. FIG. 7 is an example of a display screen 80 that is displayed on the monitor 18 in real time by the display control unit 54 in the region-of-interest detection mode. In the present embodi- ment, a lesion portion 77 of the observation target is highlighted as the region-of-interest.

In a case of performing highlight display of the region-of-interest, the display control unit 54 first sets a highlight region for highlighting the region-of-interest based on the detection information 76A such as the endoscopic image 75, the position, the dimension, and the type of the lesion portion 77, and the first highlight level setting value. In the present embodiment, the display control unit 54 sets a highlight region 78 that has an area larger than an area of the lesion portion 77 and includes the lesion portion 77. As the highlight region 78, a square region is set. The highlight region 78 has, for example, a square outer circumference that is set at a predetermined interval from an outer circum- ference of the lesion portion 77. The highlight region 78 is not limited thereto, and may be set to a square in contact with the outer circumference of the lesion portion 77.

The display control unit 54 performs highlight display of the highlight region 78 which is set as described above by using the first highlight level setting value. That is, the display control unit 54 superimposes and displays a figure as a highlight display at a position of the highlight region 78 in the endoscopic image 75. In the present embodiment, the display control unit 54 disposes, as the highlight display in which the first highlight level setting value is used, four L-shaped FIGS. 79A to 79D (frame shape) surrounding the lesion portion 77 at each corner of the highlight region 78. The first highlight level setting value includes values such as a shape, a color, and a length and a thickness of each line of the L-shaped FIGS. 79A to 79D.

In FIG. 7, FIG. 8, FIG. 10, and FIG. 12, for convenience of illustration, a color difference between the L-shaped FIGS. 79A to 79D and the other portions in the endoscopic image 75 is represented by the presence or absence of shading. On the other hand, actually, each shaded portion is colored with one color, and each of the L-shaped FIGS. 79A to 79D is one line. In addition, in FIG. 7, FIG. 10, and FIG. 13, a two-dot chain line representing the highlight region 78 is illustrated for convenience of explaining arrangement of the L-shaped FIGS. 79A to 79D, and is not actually dis- played. After the highlight region 78 is set, the display control unit 54 resets the highlight region 78 according to a change amount of the lesion portion 77 in the endoscopic image 75, and displays the L-shaped FIGS. 79A to 79D in accordance with the position of the reset highlight region 78.

In addition, the L-shaped FIGS. 79A to 79D as the highlight display have a display form different from display forms of other portions of the endoscopic image 75. The display control unit 54 displays the L-shaped FIGS. 79A to 79D, for example, in a color having a hue different from a color which is generally and mostly included in the endo- scopic image. In addition, the color of the L-shaped FIGS. 79A to 79D may be set according to an input operation by a user.

On the other hand, the highlight level setting unit 72 changes the setting from the first highlight level setting value which is preset in the initial setting or the like to the second highlight level setting value by user input informa- tion to be described later. The first highlight level setting value may be set in advance, for example, at the time of product shipment of the processor device 16 or may be set by the user at the time of using the processor device 16.

The user input reception unit 57 receives user input information by an input operation of a user. In a case where the user input reception unit 57 receives the user input information, as an example illustrated in FIG. 8, the display control unit 54 displays a setting change screen 81 on the monitor 18. The setting change screen 81 may be switched, for example, from the display screen 80 of the endoscopic image 75 in the region-of-interest detection mode by an input operation of the console 19, or may be displayed on the monitor 18 in a case where image diagnosis by the endoscope system 10 is started.

In the setting change screen 81, in order to perform a setting change from the first highlight level setting value to the second highlight level setting value, a highlight display example 82A before a setting change, a highlight display example 82B after a setting change, and selection buttons 83A and 83B for selecting whether or not to execute a setting change are displayed.

The highlight display example 82A before a setting change is an example in a case where highlight display of the lesion portion 77 is performed using the first highlight level setting value, and the highlight display example 82B after a setting change is an example in a case where highlight display of the lesion portion 77 is performed using the second highlight level setting value. The user can confirm the highlight display examples 82A and 82B and determine whether or not to perform a setting change.

Figure 8:
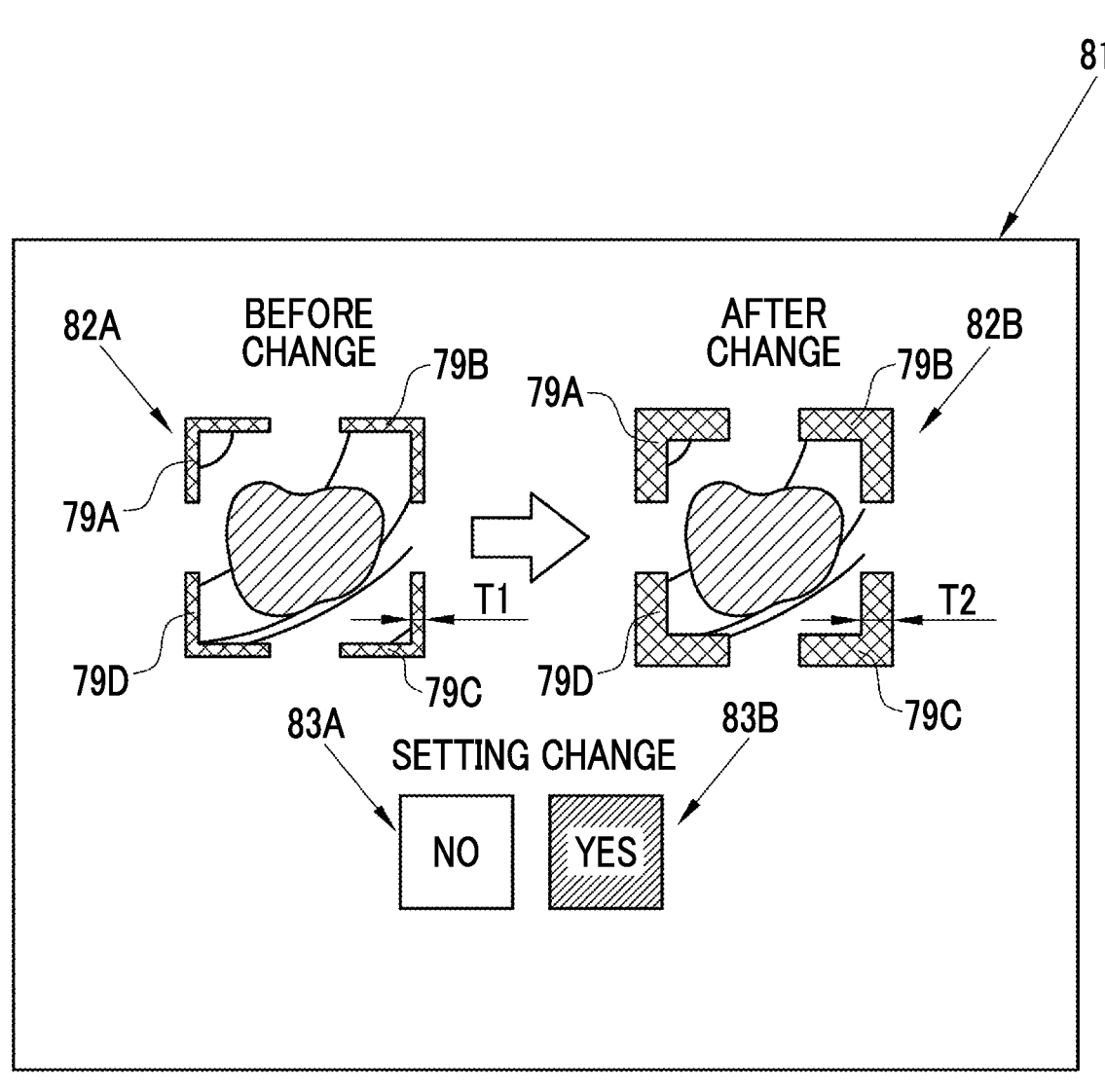
FIG. 8 is an explanatory diagram illustrating a setting change screen for performing a setting change from a first highlight level setting value to a second highlight level setting value.

A text "NO" indicating not to perform a setting change is added to the selection button 83A, and a text "YES" indicating to perform a setting change is added to the selection button 83B. The state illustrated in FIG. 8 illustrates a state where the selection button 83B is selected. In a case where the selection button 83B is selected by an input operation of the console 19, the user input reception unit 57 receives the user input information for performing a setting change of the highlight display.

The user input reception unit 57 receives the user input information by the input operation of the user, and then outputs the user input information to the highlight level setting unit 72. As the input operation for selecting any one of the selection button 83A or the selection button 83B, an input is performed by putting a cursor on one of the selection buttons 83A and 83B by an input device such as a mouse and performing a so-called click operation. Further, also in the following embodiments, in a case where any one of a plurality of selection buttons is selected, the same operation is performed.

On the other hand, the user input reception unit 57 does not receive the user input information by the input operation of the user, that is, in a case where an input operation of the user is not performed, or in a case where the user selects the selection button 83A not to perform a setting change of the highlight display, the user input reception unit 57 determines that the user input information is not received, and does not output the user input information to the highlight level setting unit 72.

In a case where the user input information is input, the highlight level setting unit 72 performs a setting change from the first highlight level setting value which is preset in the initial setting or the like to the second highlight level setting value for changing the shape of the highlight display to be different. In a case where the endoscopic image is stored in the image storage unit 56, the highlight level setting unit 72 outputs the endoscopic image 75 with which the second highlight level setting value is associated to the image storage control unit 55. In this case, the second highlight level setting value is included in the detection information 76B (corresponding to highlight display information in the claims) recorded as the association information of the endoscopic image 75. The detection information 76B is obtained by changing the first highlight level setting value of the detection information 76A to the second highlight level setting value.

In the present embodiment, in a case where the highlight level setting unit 72 performs a setting change from the first highlight level setting value to the second highlight level setting value, the highlight level setting unit 72 changes a thickness of a line of each of the L-shaped FIGS. 79A to 79D, as a change of the shape of the highlight display. In addition, in the present embodiment, the highlight display according to the second highlight level setting value is set to have a highlight level higher than a highlight level of the highlight display according to the first highlight level setting value. For example, in the highlight display using the first highlight level setting value, the thickness T1 of the line of each of the L-shaped FIGS. 79A to 79D is T1=2 pixels (refer to FIG. 8), and in the highlight display using the second highlight level setting value, the thickness T2 of the line of each of the L-shaped FIGS. 79A to 79D is T2=5 pixels (refer to FIG. 8). Note that 1 pixel is a length of one pixel when the display is displayed.

Considering that the first highlight level setting value is used in a case where the endoscopic image 75 on which the highlight display of the region-of-interest is superimposed is displayed in real time and the second highlight level setting value is used in a case where the endoscopic image is displayed for viewing of a still image, a report, a presentation material, or the like, the thicknesses T1 and T2 of the lines are set.

The image storage control unit 55 performs control related to the endoscopic image to be stored in the image storage unit 56. For example, the image storage control unit 55 performs control to be described later each time an image storage instruction is input in the region-of-interest detection mode.

In a case of storing the endoscopic image 75, the image storage control unit 55 associates the detection information 76B including the second highlight level setting value with the endoscopic image 75 and stores the endoscopic image 75 in the image storage unit 56. As will be described later, the detection information 76B is used to highlight the region-of-interest on the endoscopic image 75 by using the second highlight level setting value.

Figure 9:
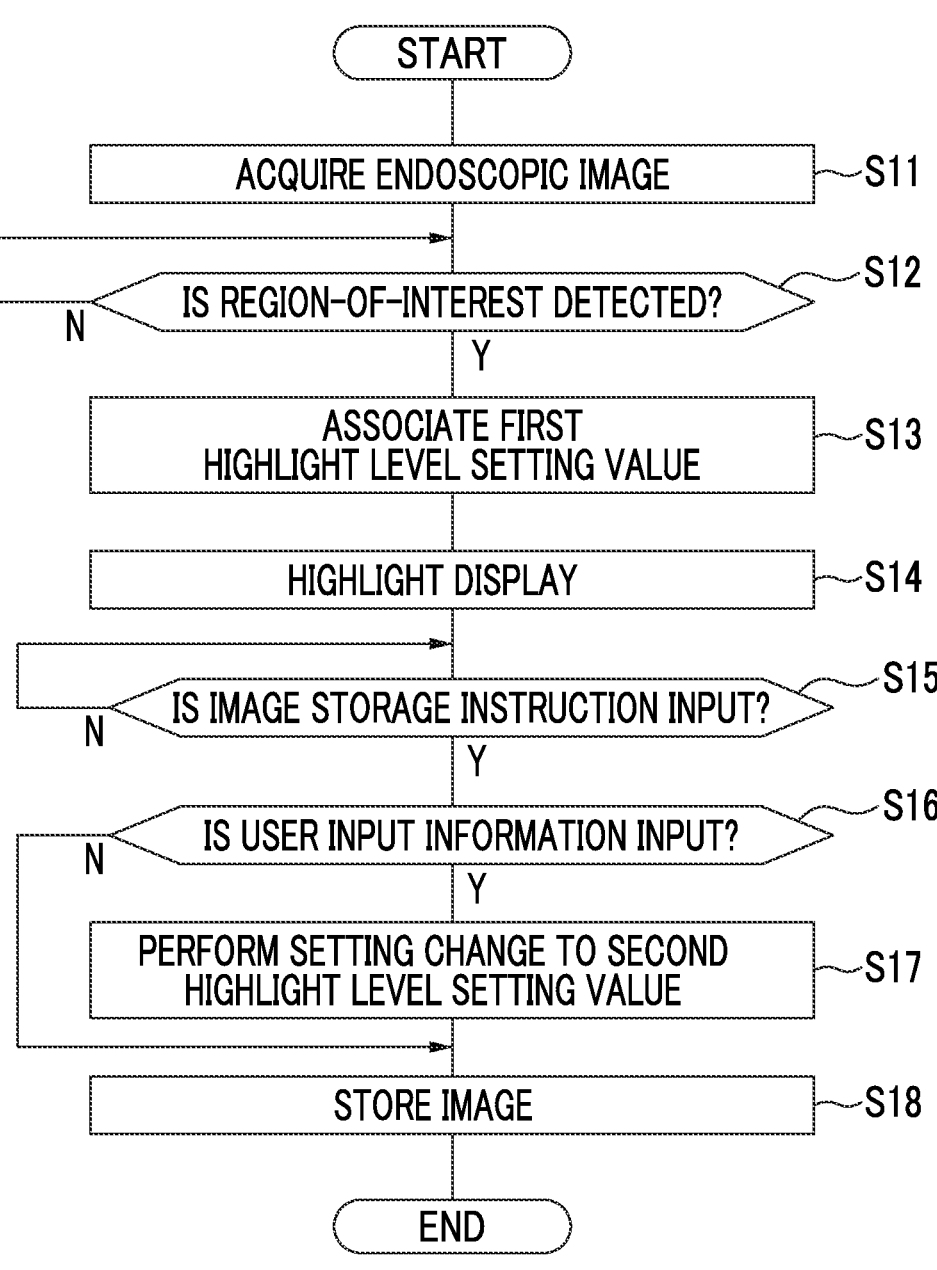
FIG. 9 is a flowchart illustrating a series of flows of a region-of-interest detection mode.
Figure 10:
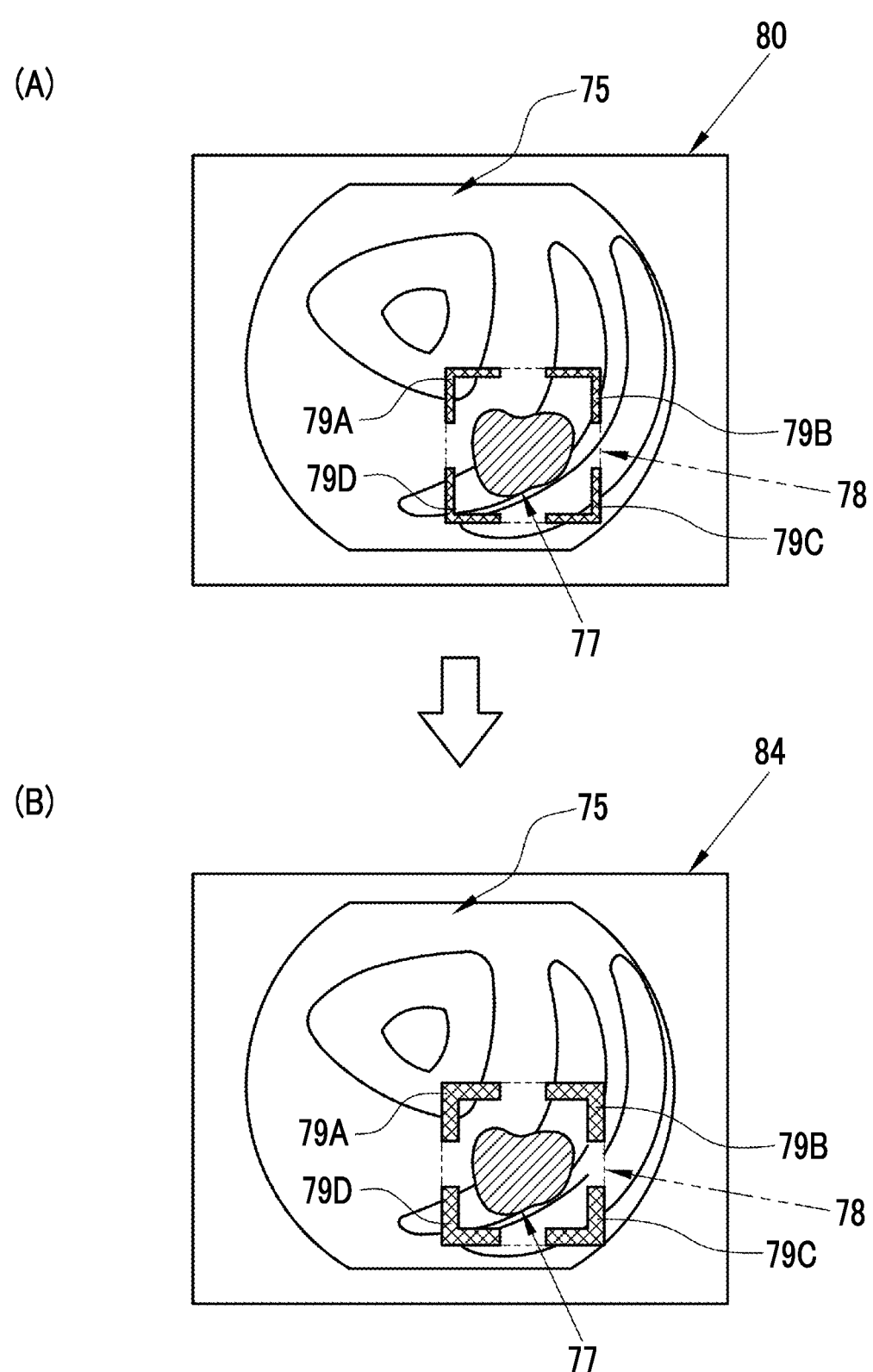
FIG. 10 is an explanatory diagram illustrating display states, and is an explanatory diagram illustrating an example of a display screen (A) for performing highlight display of a region-of-interest in real-time display and an example of a display screen (B) for viewing and displaying an endoscopic image after the endoscopic image is stored.

In the following, in the region-of-interest detection mode, a process in which the processor device 16 performs highlight display on the endoscopic image 75 by using the first highlight level setting value, associates the detection information 76B including the second highlight level setting value with the endoscopic image 75, and stores the endoscopic image 75 will be described with reference to a flowchart illustrated in FIG. 9 and an explanatory diagram illustrated in FIG. 10.

In endoscopic examination, a doctor as a user switches the observation mode to the region-of-interest detection mode by operating the mode switching unit 13c. Thereby, an observation target is illuminated with an illumination light beam for the region-of-interest detection mode. The imaging sensor 38 images the observation target illuminated with the illumination light beam for the region-of-interest detection mode, and thus the image signal acquisition unit 50 acquires an endoscopic image 75 (S11). The display control unit 54 acquires the endoscopic image 75, and displays the endoscopic image 75 in real time on the display screen 80 of the monitor 18.

The region-of-interest detection unit 71 sequentially detects a region-of-interest from the acquired endoscopic image 75. In a case where a region-of-interest is detected (Y in S12), the highlight level setting unit 72 outputs the endoscopic image 75 associated with the first highlight level setting value to the display control unit 54 (S13). The display control unit 54 superimposes and displays the L-shaped FIGS. 79A to 79D as the highlight display at a position of the highlight region 78 in the endoscopic image 75 by using the first highlight level setting value (S14, a state illustrated in FIG. 10(A)). In a case where a region-of-interest is not detected (N in S12), the display control unit 54 displays the endoscopic image 75 as it is in real time.

In a case where the freeze switch 13b is operated by a doctor during the real-time display, an image storage instruction is input to the image processing unit 53 and the image storage control unit 55. In a case where an image storage instruction is input (Y in S15) and the user input information is input (Y in S16), the highlight level setting unit 72 performs a setting change from the first highlight level setting value to the second highlight level setting value (S17). The image storage control unit 55 associates the detection information 76B including the second highlight level setting value with the endoscopic image 75, and stores the endoscopic image 75 associated with the detection information 76B in the image storage unit 56 (S18).

In a case where an image storage instruction is not input (N in S15), the image storage control unit 55 does not store the endoscopic image 75. In addition, in a case where an image storage instruction is input (Y in S15) and the user input information is not input (N in S16), that is, in a case where the user input reception unit 57 does not receive the user input information, the image storage control unit 55 may associate the detection information 76A including the first highlight level setting value with the endoscopic image 75, and store the endoscopic image 75 associated with the detection information 76A in the image storage unit 56 without performing a setting change from the first highlight level setting value to the second highlight level setting value (S18).

Thereby, in a case of displaying the endoscopic image 75 in real time, highlight display is performed using the first highlight level setting value having a low highlight level (refer to FIG. 10(A)). Therefore, the L-shaped FIGS. 79A to 79D as the highlight display are not too obtrusive and do not hinder a diagnosis of a doctor. On the other hand, in a case of storing the endoscopic image 75 in the image storage unit 56, the image storage control unit 55 associates the second highlight level setting value with the endoscopic image 75 and stores the endoscopic image 75 associated with the second highlight level setting value. Therefore, after the endoscopic examination, in a case where the endoscopic image 75 is used for viewing of a still image, a report, a presentation material, or the like, for example, as in the display screen 84 illustrated in FIG. 10(B), it is possible to reliably perform highlight display of the region-of-interest.

Figure 11:
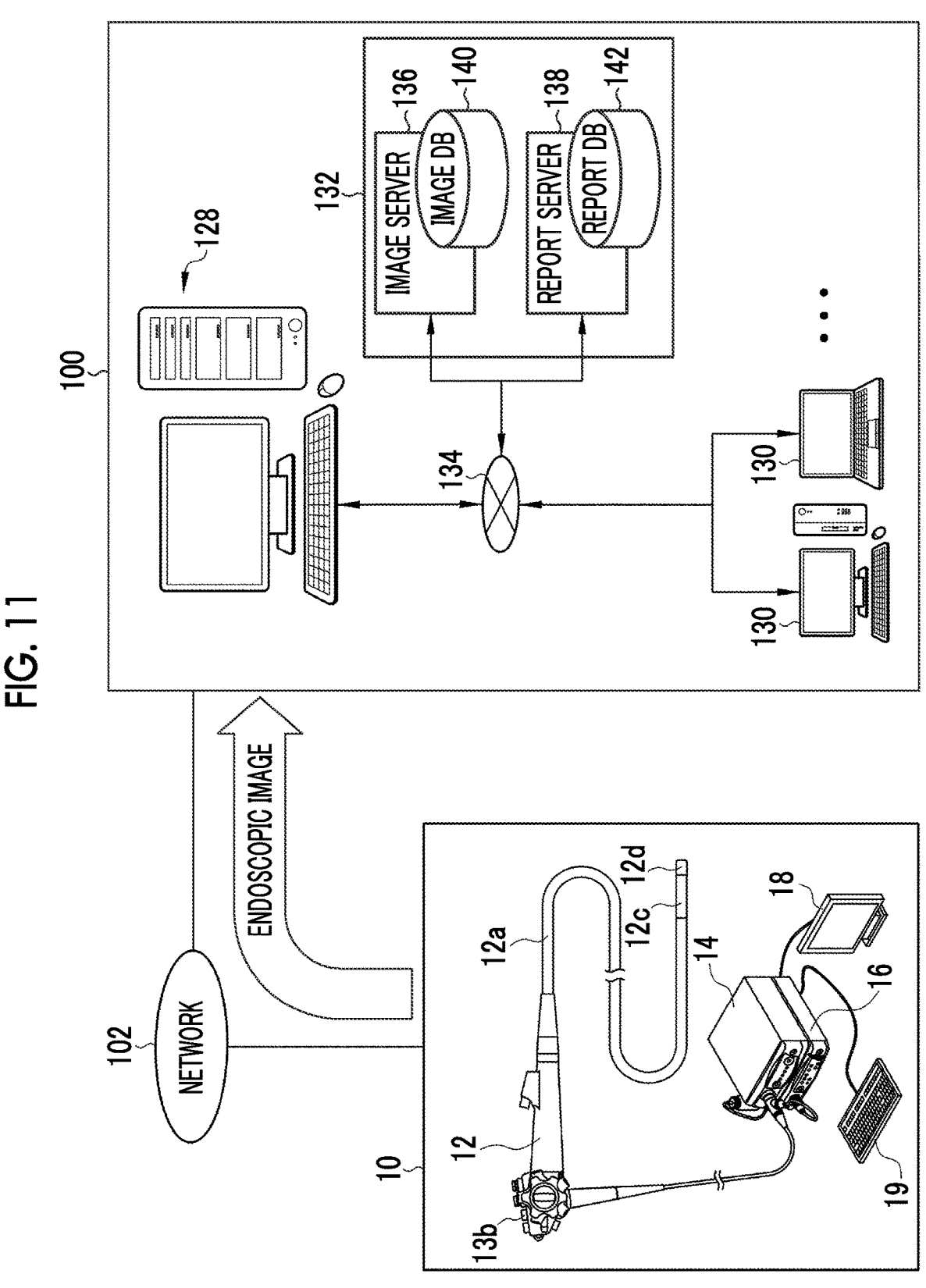
FIG. 11 is an explanatory diagram illustrating a schematic configuration of an examination image viewing support system.

An example of a case where the endoscopic image 75 stored in the image storage unit 56 is used for viewing of a still image, a report, or the like will be described below. As illustrated in FIG. 11, the endoscope system 10 is connected to an examination image viewing support system 100 via a network 102. The network 102 is, for example, a local area network (LAN) in a hospital.

As described above, the endoscopic image 75 which is imaged by the endoscope system 10 is temporarily stored in the image storage unit 56 and then stored in the examination image viewing support system 100. The examination image viewing support system 100 includes an examination image viewing support server 128, a client terminal 130, and a server group 132, which are connected to each other via a network 134 such as a LAN. The examination image viewing support server 128 generates and updates an examination image display screen for displaying the endoscopic image 75 based on a request from the client terminal 130, and distributes the examination image display screen to the client terminal 130.

The server group 132 includes an image server 136 and a report server 138. The image server 136 includes an image database (hereinafter, referred to as an image DB) 140. The endoscopic image 75 transmitted from the endoscope system 10 is stored in the image DB 140. The report server 138 includes a report database (hereinafter, referred to as a report DB) 142. The report DB 142 stores an examination report 144 created in accordance with an execution of the endoscopic examination (refer to FIG. 11). The image DB 140 and the report DB 142 are databases on which searching can be performed by a keyword such as patient identification data (ID) assigned to each patient or an examination ID assigned to each endoscopic examination.

The examination report 144 is a report in which a doctor such as an examiner who performs an endoscopic examination views the endoscopic image 75 and summarizes a medical note and the like. The endoscopic image 75, which is a basis of the note, is attached to the examination report 144.

The client terminal 130 is a terminal for viewing the endoscopic image 75 and the examination report 144, and is used in a case where an examiner views the endoscopic image 75 or creates the examination report 144 after the examination is completed. In addition, the client terminal 130 is used in a case where a doctor in a medical department who requests the endoscopic examination views the endoscopic image 75 and the examination report 144. The client terminal 130 is, for example, a laptop computer or a desktop personal computer. In a case of performing follow-up observation or the like, the client terminal 130 that is used by a doctor accesses the examination image viewing support server 128, reads the stored endoscopic image 75 and the stored examination report 144, and performs viewing.

Figure 12:
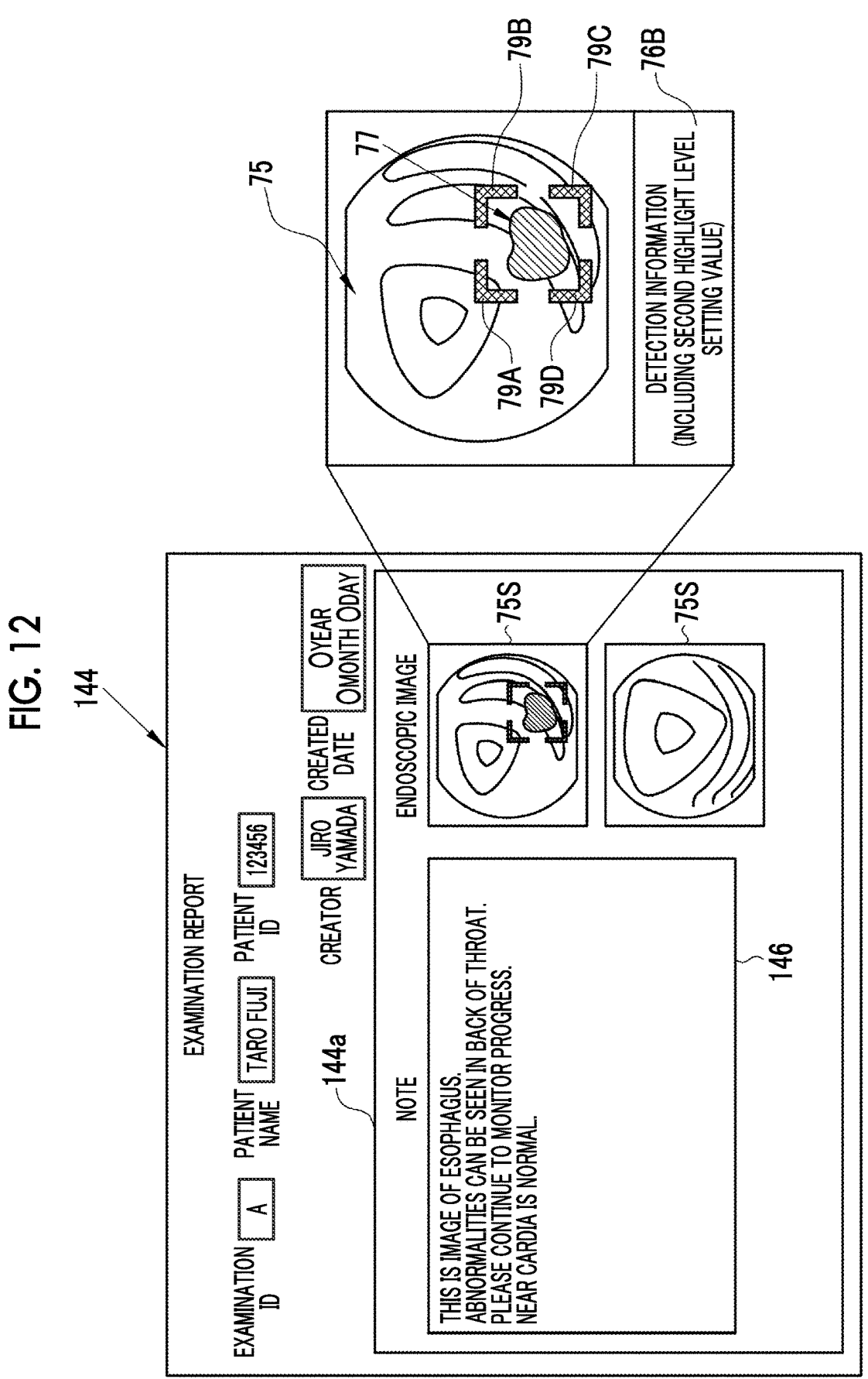
FIG. 12 is an explanatory diagram illustrating an example of an examination report.
Figure 13:
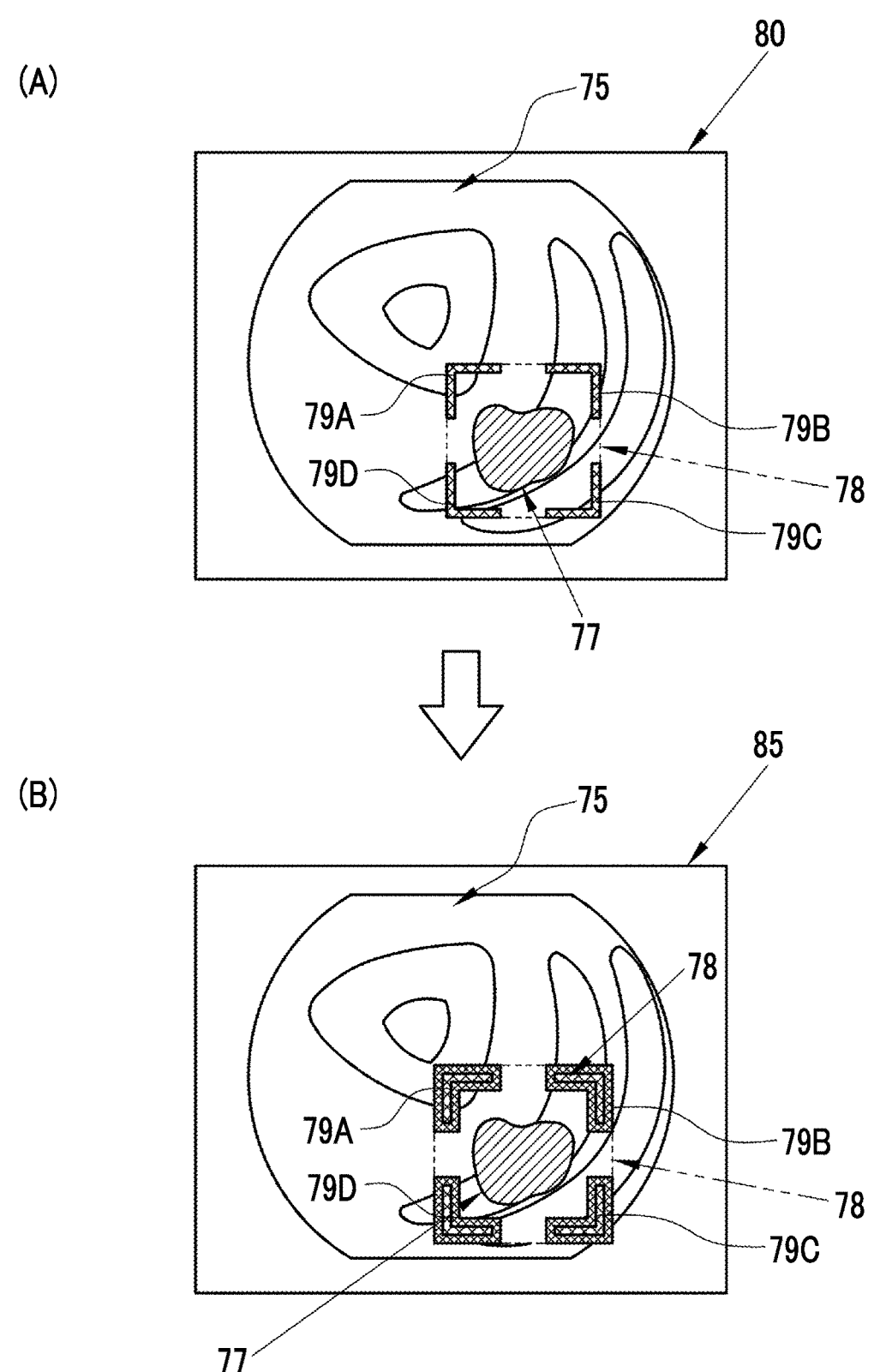
FIG. 13 is an explanatory diagram illustrating display states according to a second embodiment, and is an explanatory diagram illustrating an example of a display screen (A) for performing highlight display of a region-of-interest in real-time display and an example of a display screen (B) for viewing and displaying an endoscopic image after the endoscopic image is stored.

As illustrated in FIG. 12, the examination report 144 includes a report body 144a, examination identification information, patient identification information, and creator information. The report body 144a includes a note 146 of an examiner of the endoscopic examination and the endoscopic image 75 attached to the examination report 144. The endoscopic image 75 is an endoscopic image 75 that is a basis of the note 146.

In creation of the examination report 144, an examiner inputs a note 146 while observing a plurality of endoscopic images 75 obtained by performing endoscopic examination, and attaches the endoscopic images 75 as a basis of the note to the examination report 144. In a case where the endoscopic image 75 is attached to the examination report 144, for example, the endoscopic image 75 is converted into a form of a thumbnail image 75S. The present invention is not limited thereto. For example, the endoscopic image 75 may be inserted into the examination report 144 as it is, or the note 146 and the endoscopic image 75 may be switched in a separate window.

As described above, in a case where the endoscopic image 75 is viewed on the client terminal 130 or is used for creating the examination report 144, highlight display of the endoscopic image 75 is performed using the detection information 76B including the second highlight level setting value.

The second highlight level setting value for changing the shape of the highlight display to be different from the shape according to the first highlight level setting value is used. Therefore, it is possible to reliably perform highlight display of the region-of-interest. In addition, in the present embodiment, the highlight display according to the second highlight level setting value is set to have a highlight level higher than a highlight level of the highlight display according to the first highlight level setting value. Therefore, it is possible to reliably perform highlight display of the lesion portion 77 as the region-of-interest, and a doctor can easily notice that a region-of-interest exists in the medical image. In addition, in the highlight display according to the second highlight level setting value, as compared with the highlight display according to the first highlight level setting value, the thickness of the line of each of the L-shaped FIGS. 79A to 79D is changed. Therefore, it is possible to more reliably perform highlight display of the region-of-interest.

Second Embodiment

In the first embodiment, in a case where the setting change from the first highlight level setting value to the second highlight level setting value is performed, as a change of the shape of the highlight display, a thickness of a line of a frame shape surrounding the region-of-interest is changed. On the other hand, the present invention is not limited thereto. As a change of the shape of the highlight display, the number of the lines of the frame shape surrounding the region-of-interest may be changed. FIG. 13(A) illustrates an example of performing highlight display of the lesion portion 77 in the endoscopic image 75 by using the first highlight level setting value, and FIG. 13(B) illustrates an example performing highlight display of the lesion portion 77 in the endoscopic image 75 by using the second highlight level setting value for changing the number of the lines of the frame shape to be different from the number of the lines of the frame shape according to the first highlight level setting value. In FIG. 13(A) and FIG. 13(B), a difference in colors of the lines is represented by a size of a shaded mesh, and each shaded portion is actually colored with one color.

In the present embodiment, in a case where the highlight level setting unit 72 performs a setting change from the first highlight level setting value to the second highlight level setting value, the highlight level setting unit 72 changes the number of the lines of the L-shaped FIGS. 79A to 79D, as a change of the shape of the highlight display. In addition, in the present embodiment, the highlight display according to the second highlight level setting value is set to have a highlight level higher than a highlight level of the highlight display according to the first highlight level setting value, that is, to have the number of the lines of each of the L-shaped FIGS. 79A to 79D that is larger than the number of the lines according to the first highlight level setting value. Other configurations are the same as those of the endoscope system 10 according to the first embodiment.

For example, as in the display screen 80 illustrated in FIG. 13(A), in the highlight display using the first highlight level setting value, each of the L-shaped FIGS. 79A to 79D is formed of one line as in the first embodiment. On the other hand, as in the display screen 85 illustrated in FIG. 13(B), in the highlight display using the second highlight level setting value, each of the L-shaped FIGS. 79A to 79D is formed of double lines including a single line and lines surrounding the line. Further, in the present embodiment, each of the L-shaped FIGS. 79A to 79D is formed of double lines having different colors from each other.

Similar to the first embodiment, in the image processing unit 53, the display control unit 54, and the image storage control unit 55, highlight display is performed on the endoscopic image 75 by using the first highlight level setting value, and the endoscopic image 75 is stored by being associated with the detection information 76B including the second highlight level setting value. In a case of displaying the endoscopic image 75 in real time, highlight display is performed using the first highlight level setting value having a low highlight level (refer to FIG. 13(A)). Therefore, the L-shaped FIGS. 79A to 79D as the highlight display are not too obtrusive. On the other hand, a setting change to the second highlight level setting value is performed so as to change the number of the lines of the frame shape to be different from the number of the lines of the frame shape according to the first highlight level setting value. Therefore, after the endoscopic examination, in a case where the endoscopic image 75 is used for viewing of a still image, a report, or the like, for example, as in the display screen 85 illustrated in FIG. 13(B), it is possible to reliably perform highlight display of the region-of-interest.

Third Embodiment

Figure 14A:
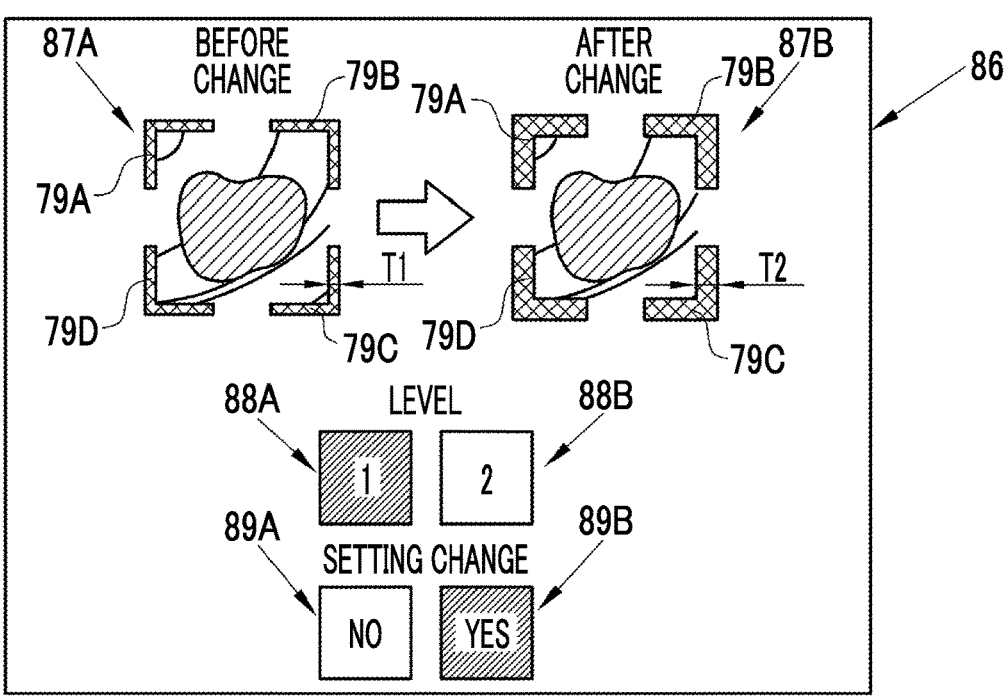
FIGS. 14A and 14B are an explanatory diagram illustrating an example of a setting change screen according to a third embodiment, and is an explanatory diagram illustrating an example of a case FIG. 14A where a highlight display example after a setting change in a first stage is displayed and an example of a case FIG. 14B where a highlight display example after a setting change in a second stage is displayed.
Figure 14B:
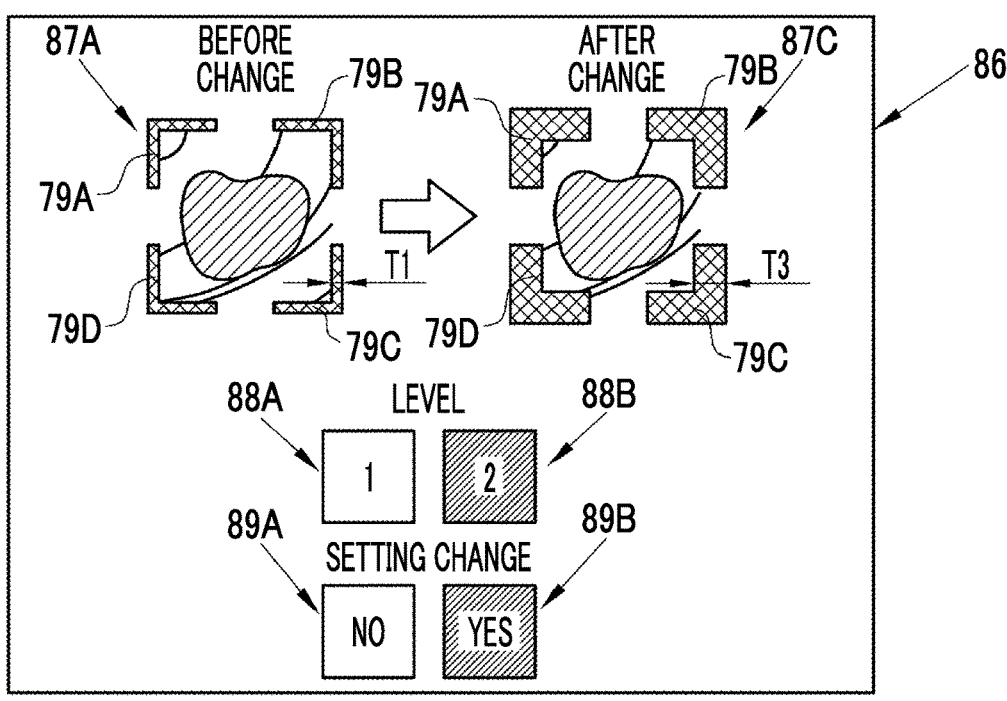

In the first embodiment and the second embodiment, in a case where a setting change from the first highlight level setting value to the second highlight level setting value is performed, as a change of the shape of the highlight display, an example in which the setting change is performed in one stage has been described. On the other hand, the present invention is not limited thereto. The setting change may be performed in a plurality of stages. In the present embodiment, for example, in a case where the user input reception unit 57 receives the user input information, the display control unit 54 displays the setting change screen 86 as illustrated in FIG. 14A and FIG. 14B on the monitor 18.

On the setting change screen 86, a highlight display example 87A before a setting change, highlight display examples 87B and 87C after a setting change, stage selection buttons 88A and 88B for selecting a stage (level) of the setting change, and execution selection buttons 89A and 89B for selecting whether or not to perform a setting change are displayed.

The highlight display example 87A before a setting change is an example in a case where highlight display of the lesion portion 77 is performed by using the first highlight level setting value. In the above-described setting change in a plurality of stages, in the example illustrated in FIG. 14A, the highlight display example 87B after a setting change in a first stage is displayed, and in the example illustrated in FIG. 14B, the highlight display example 87C after a setting change in second stage is displayed. A text "1" indicating a setting change in the first stage is added to the stage selection button 88A, and a text "2" indicating a setting change in the second stage is added to the stage selection button 88B. The example illustrated in FIG. 14A illustrates a state where the stage selection button 88A is selected, and the example illustrated in FIG. 14B illustrates a state where the stage selection button 88B is selected.

In the present embodiment, in a case where the highlight level setting unit 72 performs a setting change from the first highlight level setting value to the second highlight level setting value, the highlight level setting unit 72 changes a thickness of a line of each of the L-shaped FIGS. 79A to 79D, as a change of the shape of the highlight display, and further changes the thickness of the line according to the stage of the setting change. In addition, the highlight display according to the second highlight level setting value is set to have a highlight level higher than a highlight level of the highlight display according to the first highlight level setting value. Further, in the setting change, the highlight level in the second stage is set to be higher than the highlight level in the first stage.

For example, in the highlight display using the first highlight level setting value, the thickness T1 of the line of each of the L-shaped FIGS. 79A to 79D is T1=2 pixels (the highlight display example 87A illustrated in FIG. 14A). In the setting change in the first stage and the highlight display using the second highlight level setting value, the thickness T2 of the line of each of the L-shaped FIGS. 79A to 79D is T2=5 pixels (the highlight display example 87B illustrated in FIG. 14A). Further, in the setting change in the second stage and the highlight display using the second highlight level setting value, the thickness T3 of the line of each of the L-shaped FIGS. 79A to 79D is T3=7 pixels (the highlight display example 87C illustrated in FIG. 14B).

The execution selection buttons 89A and 89B are the same as the selection buttons 83A and 83B according to the first embodiment. In states illustrated in FIG. 14A and FIG. 14B, a state where the execution selection button 89B is selected is illustrated.

In a case where the user selects the stage selection button 88A or 88B, a setting change in the first stage or a setting change in the second stage is selected. Thereby, the user can confirm the highlight display example 87A, 87B, or 87C and determine whether or not to perform a setting change. In a case where any one of the stage selection button 88A or the stage selection button 88B is selected by an input operation of the console 19 and the execution selection button 89B is selected, the user input reception unit 57 receives the user input information for performing a setting change of the highlight display and setting a stage of the setting change. In a case where the execution selection button 89A is selected, the user input reception unit 57 determines that the user input information is not received, and does not output the user input information to the highlight level setting unit 72.

The user input reception unit 57 receives the user input information by the input operation of the user, and then outputs the user input information to the highlight level setting unit 72. In a case where the user input information is input, the highlight level setting unit 72 performs a setting change from the first highlight level setting value to the second highlight level setting value according to the stage of the setting change. As in the first embodiment and the second embodiment, in a case of storing the endoscopic image 75, the image storage control unit 55 associates the detection information 76B including the second highlight level setting value with the endoscopic image 75 and stores the endoscopic image 75 associated with the detection information 76B in the image storage unit 56.

Similar to the first embodiment and the second embodiment, in the image processing unit 53, the display control unit 54, and the image storage control unit 55, highlight display is performed on the endoscopic image 75 by using the first highlight level setting value, and the endoscopic image 75 is stored by being associated with the detection information 76B including the second highlight level setting value. In a case of displaying the endoscopic image 75 in real time, highlight display is performed using the first highlight level setting value having a low highlight level. Therefore, the L-shaped FIGS. 79A to 79D as the highlight display are not too obtrusive. On the other hand, a setting change to the second highlight level setting value is performed so as to change the shape of the highlight display to be different from the shape of the highlight display according to the first highlight level setting value. Therefore, after the endoscopic examination, in a case where the endoscopic image 75 is used for viewing of a still image, a report, or the like, it is possible to reliably perform highlight display of the region-of-interest. Further, as a change of the shape of the highlight display, a setting change can be performed in a plurality of stages. Therefore, in a case where the highlight display is performed by using the second highlight level setting value, it is possible to highlight the region-of-interest at a highlight level more suitable for preference of the user.

In the third embodiment, in a case where a setting change from the first highlight level setting value to the second highlight level setting value is performed, as a change of the shape of the highlight display, the setting change is performed in two stages. On the other hand, the present invention is not limited thereto. The setting change may be performed in three or more stages. In this case, as in the third embodiment, preferably, a setting change screen or the like is displayed, an input operation is performed by the user, and any one of three or more stages of the setting change is selected by the user.

Figure 15:
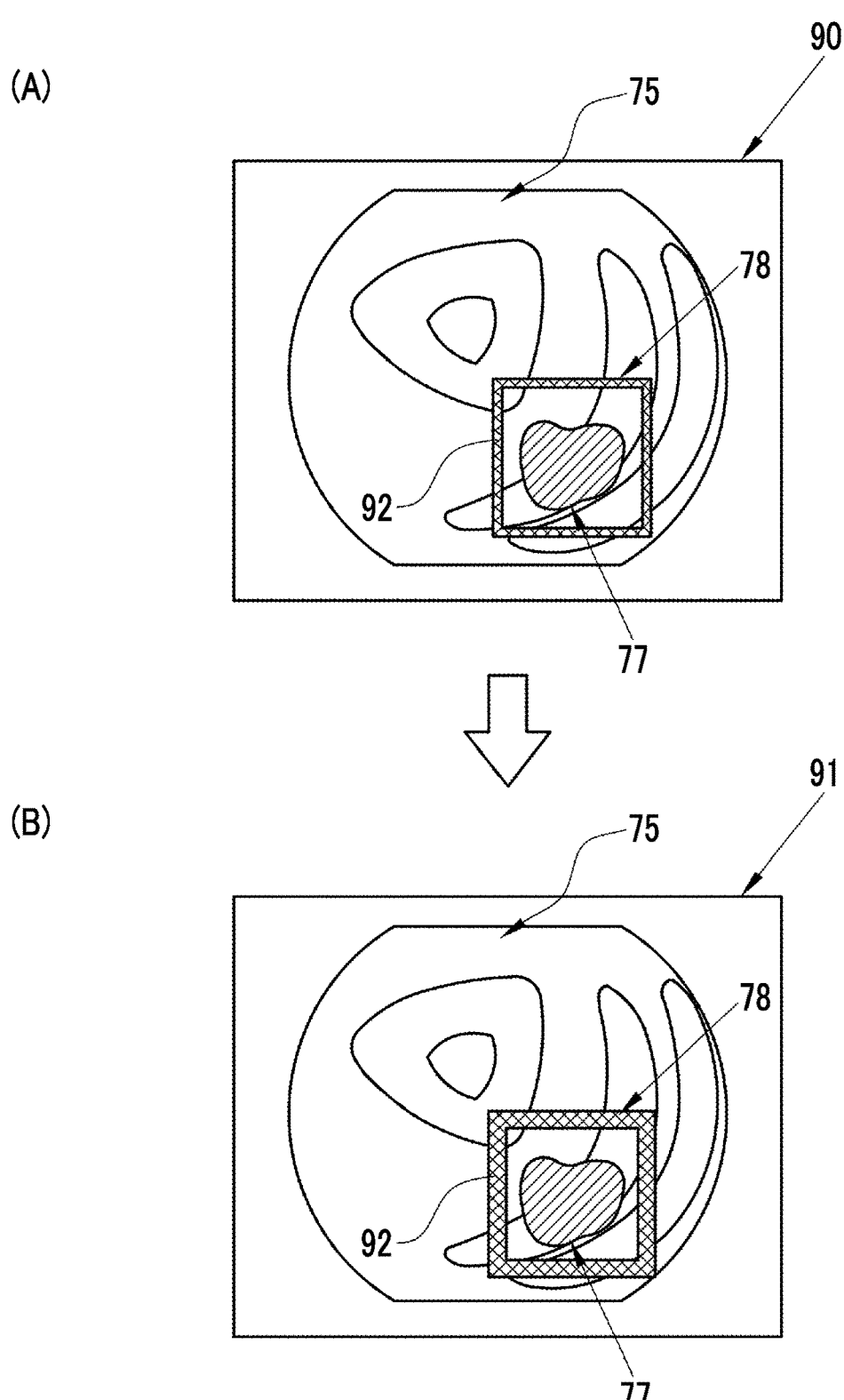
FIG. 15 is an explanatory diagram illustrating, as a modification example, an example in which a highlight display includes a quadrangular frame-shaped figure surrounding a lesion portion.

In addition, in each of the above-described embodiments, an example in which the display control unit 54 superimposes the four L-shaped FIGS. 79A to 79D, which are the highlight display and surround the lesion portion 77, on the endoscopic image 75 and displays the endoscopic image 75 has been described. On the other hand, the present invention is not limited thereto. The highlight display may be formed of one frame shape. In the display screen 90 illustrated in FIG. 15(A) and the display screen 91 illustrated in FIG. 15(B), as the highlight display, a quadrangular frame-shaped FIG. 92 surrounding the lesion portion 77 is superimposed and displayed at a position of the highlight region 78. FIG. 15(A) illustrates an example of performing highlight display of the lesion portion 77 by using the first highlight level setting value, and FIG. 15(B) illustrates an example performing highlight display of the lesion portion 77 in the endoscopic image 75 by using the second highlight level setting value for changing a thicknesses of a line of the FIG. 92 to be different from a thicknesses of a line of the FIG. 92 according to the first highlight level setting value. The present invention is not limited thereto. As in the second embodiment, in a case of performing a setting change from the first highlight level setting value to the second highlight level setting value, the number of lines of the FIG. 92 may be changed, the setting change may be performed in a plurality of stages.

In each of the above-described embodiments, the user input reception unit 57 receives the user input information by an input operation of the console 19. On the other hand, the present invention is not limited thereto. The user input information may be received by various input devices such as a pressure detection device such as a mouse, a foot pedal or a touch pad, a keyboard, a voice input device, and a touch panel input device. Alternatively, any one of the operation buttons provided on the endoscope 12 may be used as an operation button for selecting a setting change, and the user input reception unit 57 receives the user input information in a case where an input operation is performed by the operation button.

In each of the above-described embodiments, the detection information 76B (highlight display information) includes information such as position information, dimensions, and a lesion type of a lesion portion as a region-of-interest. On the other hand, the present invention is not limited thereto. The detection information may include any one of a malignancy or a benignancy of the lesion portion, a degree of progression of the lesion portion, the presence or absence of treatment, a note, a part or an organ in which the lesion portion exists, or patient information.

In each of the above-described embodiments, the image storage control unit 55 associates the detection information 76B including the second highlight level setting value with the endoscopic image 75 and stores the endoscopic image 75 in the image storage unit 56 of the processor device 16. On the other hand, the present invention is not limited thereto. In a case where the processor device 16 can be connected to a network, instead of or in addition to the image storage unit 56, the endoscopic image 75 may be stored in an image storage server (not illustrated) connected to the network. Further, in each of the above-described embodiments, a still image is stored as the endoscopic image 75. On the other hand, the present invention is not limited thereto, and a moving image may be used.

In each of the above-described embodiments, the figure as the highlight display has a frame shape including the L-shaped FIGS. 79A to 79D or a square frame shape. On the other hand, the present invention is not limited thereto. The figure as the highlight display may have a frame shape that can surround the region-of-interest, such as a polygon other than a rectangle (quadrangular), a circle, or an ellipse. The highlight display of the region-of-interest is not limited thereto. The highlight display may be image processing which allows the highlight region to be visually distinguished from the surroundings, such as chroma saturation change processing, contrast processing, negative/positive inversion processing, and filtering processing. Alternatively, the highlight display of the region-of-interest by image processing may be combined with the highlight display by a figure surrounding the lesion portion in each of the above-described embodiments.

In each of the above-described embodiments, the four-color LEDs 20a to 20d are used to illuminate the observation target. On the other hand, a laser light source and a phosphor may be used to illuminate the observation target. In addition, in each of the above-described embodiments, the four-color LEDs 20a to 20d are used to illuminate the observation target. On the other hand, a white light source such as a xenon lamp and a rotation filter may be used to illuminate the observation target. In addition, instead of the color imaging sensor 38, a monochrome imaging sensor may be used to perform imaging of the observation target.

In the above-described embodiments, the medical image processing apparatus according to the present invention is applied to the endoscope system that acquires an endoscopic image as a medical image. On the other hand, the medical image processing apparatus according to the present invention can be applied to various endoscope systems such as capsule endoscopes, and can also be applied to various medical imaging apparatuses that acquire, as other medical images, an X-ray image, a CT image, an MR image, an ultrasound image, a pathological image, a positron emission tomography (PET) image, and the like.

In the embodiment, a hardware structure of the processing unit that executes various processing, such as the image processing unit 53, the display control unit 54, the image storage control unit 55, or the user input reception unit 57, is realized by the following various processors. The various processors include a central processing unit (CPU) which is a general-purpose processor that functions as various processing units by executing software (program), a graphical processing unit (GPU), a programmable logic device (PLD) such as a field programmable gate array (FPGA) which is a processor capable of changing a circuit configuration after manufacture, a dedicated electric circuit which is a processor having a circuit configuration specifically designed to execute various processing, and the like.

One processing unit may be configured by one of these various processors, or may be configured by a combination of two or more processors having the same type or different types (for example, a combination of a plurality of FPGAs, a combination of a CPU and an FPGA, a combination of a CPU and a GPU, or the like). Further, the plurality of processing units may be configured by one processor. As an example in which the plurality of processing units are configured by one processor, firstly, as represented by a computer such as a client and a server, a form in which one processor is configured by a combination of one or more CPUs and software and the processor functions as the plurality of processing units is adopted. Secondly, as represented by a system on chip (SoC) or the like, a form in which a processor that realizes the function of the entire system including the plurality of processing units by one integrated circuit (IC) chip is used is adopted. As described above, the various processing units are configured by using one or more various processors as a hardware structure.

Further, as the hardware structure of the various processors, more specifically, an electric circuit (circuitry) in which circuit elements such as semiconductor elements are combined is used.

EXPLANATION OF REFERENCES

10: endoscope system
12: endoscope
12a: insertion part
12b: operating part
12c: bendable part
12d: tip part
13a: angle knob
13b: freeze switch
13c: mode switching unit
13d: zoom operating part
14: light source device
16: processor device
18: monitor
19: console
20: light source unit
20a: V-LED
20b: B-LED
20c: G-LED
20d: R-LED
22: light source control unit
23: wavelength cut filter
24: light guide
30a: Illumination optical system
30b: imaging optical system
32: Illumination lens
34: objective lens
36: magnification optical system
36a: zoom lens
36b: lens drive unit
38: imaging sensor
40: CDS circuit
42: AGC circuit
44: A/D conversion circuit
50: image signal acquisition unit
51: digital signal processor (DSP)
52: noise reduction unit
53: image processing unit

54: display control unit
55: image storage control unit
56: image storage unit
57: user input reception unit
58: normal mode image processing unit
59: special mode image processing unit
60: region-of-interest detection mode image processing unit
70: detection image processing unit
71: region-of-interest detection unit
72: highlight level setting unit
75: endoscopic image
75S: thumbnail image
76A: detection information
76B: detection information
77: lesion portion
78: highlight region
79A to 79D: L-shaped FIGS.
80, 84, 85, 90, 91: display screen
81, 86: setting change screen
82A, 82B, 87A, 87B, 87C: highlight display example
83A, 83B: selection button
84, 85: display screen
88A, 88B: stage selection button
89A, 89B: execution selection button
92: FIG.
100: examination image viewing support system
102: network
128: examination image viewing support server
130: client terminal
132: server group
134: network
136: image server
138: report server
140: image database
142: report database
144: examination report
144*a*: report body
146: note
T1, T2, T3: thickness of line
What is claimed is:
1. A medical image processing apparatus comprising:
a processor configured to:
    acquire a medical image;
    detect a region-of-interest in the medical image;
    superimpose a highlight display for highlighting the detected region-of-interest on the medical image according to a first highlight level setting value and display the medical image on which the highlight display is superimposed on a display screen;
    receive user input information;
    perform a setting change from the first highlight level setting value to a second highlight level setting value by the user input information, the second highlight level setting value being different from the first highlight level setting value in a shape of the highlight display; and
    associate highlight display information including the second highlight level setting value with the medical image and store the medical image associated with the highlight display information in a storage.
2. The medical image processing apparatus according to claim 1,
    wherein the second highlight level setting value is applied, in a case of viewing the medical image read from the storage, for highlighting the region-of-interest on the medical image.

3. The medical image processing apparatus according to claim 1,
    wherein the processor is configured to change a thickness of a line of a frame shape surrounding the region-of-interest, as a change of the shape of the highlight display, in a case where the setting change from the first highlight level setting value to the second highlight level setting value is performed.
4. The medical image processing apparatus according to claim 1,
    wherein the processor is configured to change the number of lines of a frame shape surrounding the region-of-interest, as a change of the shape of the highlight display, in a case where the setting change from the first highlight level setting value to the second highlight level setting value is performed.
5. The medical image processing apparatus according to claim 3,
    wherein the processor is configured to form the frame shape from a plurality of lines having different colors from each other in a case where the setting change to the second highlight level setting value is performed.
6. The medical image processing apparatus according to claim 1,
    wherein the highlight display using the second highlight level setting value has a highlight level higher than a highlight level of the highlight display using the first highlight level setting value.
7. The medical image processing apparatus according to claim 1,
    wherein the processor is configured to perform the setting change in one stage or a plurality of stages, for the setting change from the first highlight level setting value to the second highlight level setting value.
8. The medical image processing apparatus according to claim 1,
    wherein, in a case where the user input information is not received, the processor is configured to associate highlight display information including the first highlight level setting value with the medical image and store the medical image associated with the highlight display information, without performing the setting change from the first highlight level setting value.
9. The medical image processing apparatus according to claim 1,
    wherein the processor is configured to receive the user input information by an input operation of any one of a keyboard, a pressure detection device, a voice input device, or a touch panel input device.
10. The medical image processing apparatus according to claim 1, wherein
    the medical image is an endoscopic image obtained by imaging an observation target by an endoscope, and
    the processor is configured to receive the user input information by an input operation of an operation button provided on the endoscope.
11. The medical image processing apparatus according to claim 1, wherein
    the region-of-interest is a lesion portion, and
    the highlight display information includes any one of position information of the lesion portion in the medical image, dimensions of the lesion portion, a malignancy or a benignancy of the lesion portion, a degree of progression of the lesion portion, the presence or absence of treatment, a note, a part or an organ in which the lesion portion exists, or patient information.

12. An endoscope system comprising:

a light source device that emits an illumination light beam for illuminating an observation target;

an endoscope including an imaging sensor which images the observation target illuminated with the illumination light beam;

a processor; and a monitor that displays a medical image obtained by performing signal processing on an image signal which is output by the imaging sensor, wherein the processor is configured to:

acquire the medical image;

detect a region-of-interest in the medical image;

superimpose a highlight display for highlighting the detected region-of-interest on the medical image according to a first highlight level setting value and display the medical image on which the highlight display is superimposed on the monitor, receive user input information;

perform a setting change from the first highlight level setting value to a second highlight level setting value by the user input information, the second highlight level setting value being different from the first highlight level setting value in a shape of the highlight display; and associate highlight display information including the second highlight level setting value with the medical image and store the medical image associated with the highlight display information in a storage.

13. A method of operating a medical image processing apparatus, the method comprising:

acquiring a medical image;

detecting a region-of-interest in the medical image;

superimposing a highlight display for highlighting the detected region-of-interest on the medical image according to a first highlight level setting value and displaying the medical image on which the highlight display is superimposed on a display screen;

receiving user input information;

performing a setting change from the first highlight level setting value to a second highlight level setting value by the user input information, the second highlight level setting value being different from the first highlight level setting value in a shape of the highlight display; and associating highlight display information including the second highlight level setting value with the medical image and storing the medical image associated with the highlight display information in a storage.

14. A non-transitory computer readable medium for storing a computer-executable program for functioning a computer as a medical image processing apparatus that acquires a medical image and performs image processing on the medical image, the computer-executable program causing the computer to execute functions of:

acquiring the medical image;

detecting a region-of-interest in the medical image;

superimposing a highlight display for highlighting the detected region-of-interest on the medical image according to a first highlight level setting value and displaying the medical image on which the highlight display is superimposed on a display screen;

receiving user input information;

performing a setting change from the first highlight level setting value to a second highlight level setting value by the user input information, the second highlight level setting value being different from the first highlight level setting value in a shape of the highlight display; and associating highlight display information including the second highlight level setting value with the medical image and storing the medical image associated with the highlight display information in a storage.

* * * * *